(12) United States Patent
Takahashi et al.

(10) Patent No.: US 11,950,836 B2
(45) Date of Patent: Apr. 9, 2024

(54) MEDICAL DEVICE AND TREATMENT METHOD

(71) Applicant: TERUMO KABUSHIKI KAISHA, Tokyo (JP)

(72) Inventors: Yusuke Takahashi, Hadano (JP); Yukitoshi Kato, Hadano (JP); Tomoaki Takemura, Kawasaki (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 645 days.

(21) Appl. No.: 17/034,056

(22) Filed: Sep. 28, 2020

(65) Prior Publication Data

US 2021/0007790 A1   Jan. 14, 2021

Related U.S. Application Data

(63) Continuation of application No. PCT/JP2019/012383, filed on Mar. 25, 2019.

(30) Foreign Application Priority Data

Mar. 29, 2018  (JP) ................................. 2018-064006

(51) Int. Cl.
*A61B 18/14* (2006.01)
*A61B 18/00* (2006.01)

(52) U.S. Cl.
CPC .... *A61B 18/14* (2013.01); *A61B 2018/00202* (2013.01); *A61B 2018/00214* (2013.01);
(Continued)

(58) Field of Classification Search
CPC ....... A61B 18/06; A61B 18/082; A61B 18/14; A61B 18/1492; A61B 18/22;
(Continued)

(56) References Cited

U.S. PATENT DOCUMENTS 5,853,422 A * 12/1998 Huebsch ............ A61B 17/0057
                                                   606/213
6,579,311 B1   6/2003 Makower
(Continued)

FOREIGN PATENT DOCUMENTS

CN   106456324 A   2/2017
EP   3 649 962 A1   5/2020
(Continued)

OTHER PUBLICATIONS

The extended European Search Report dated Apr. 8, 2021, by the European Patent Office in corresponding European Patent Application No. 19778033.1-1122. (9 pages).
(Continued)

*Primary Examiner* — Michael F Peffley
(74) *Attorney, Agent, or Firm* — BUCHANAN INGERSOLL ROONEY PC

(57) ABSTRACT

A medical device and a treatment method, in which energy is accurately applied to a target site by suppressing a positional displacement between an expansion body and a biological tissue. The medical device includes an elongated shaft portion and an expansion body disposed in a distal portion of the shaft portion and configured to expand and contract in a radial direction. The expansion body includes a holding portion having a proximal side holding portion and a distal side holding portion configured to hold the biological tissue, and a movable portion configured to open and close the holding portion.

20 Claims, 18 Drawing Sheets

(52) U.S. Cl.
CPC .............. *A61B 2018/00357* (2013.01); *A61B 2018/1467* (2013.01)

(58) Field of Classification Search
CPC ........... A61B 2017/00247; A61B 2017/00252; A61B 2017/00862; A61B 2018/0016; A61B 2018/00202; A61B 2018/00214; A61B 2018/0022; A61B 2018/00232; A61B 2018/00267; A61B 2018/00351; A61B 2018/00357; A61B 2018/00595; A61B 2018/0212; A61B 2018/1253; A61B 2018/126; A61B 2018/142; A61B 2018/1467; A61B 2018/1475; A61B 5/021

See application file for complete search history.

(56) References Cited

U.S. PATENT DOCUMENTS

| | | | |
|---|---|---|---|
| 7,678,123 B2* | 3/2010 | Chanduszko | A61B 17/0057 606/139 |
| 8,021,359 B2* | 9/2011 | Auth | A61B 18/1492 606/41 |
| 8,043,360 B2* | 10/2011 | McNamara | A61F 2/24 623/1.15 |
| 8,882,697 B2 | 11/2014 | Celermajer et al. | |
| 2010/0049190 A1 | 2/2010 | Long et al. | |
| 2010/0057192 A1 | 3/2010 | Celermajer | |
| 2012/0165928 A1* | 6/2012 | Nitzan | A61F 2/2412 623/2.15 |
| 2014/0277410 A1 | 9/2014 | Börtlein et al. | |
| 2016/0166381 A1* | 6/2016 | Sugimoto | A61L 31/022 623/2.11 |
| 2017/0071494 A1* | 3/2017 | Solis | A61B 18/1492 |
| 2020/0261704 A1 | 8/2020 | Wang et al. | |

FOREIGN PATENT DOCUMENTS

| | | |
|---|---|---|
| JP | 2001508318 A | 6/2001 |
| JP | 2010-508093 A | 3/2010 |
| JP | 2012050538 A | 3/2012 |
| WO | 2014/150106 A1 | 9/2014 |
| WO | 2019085841 A1 | 5/2019 |

OTHER PUBLICATIONS

English Translations of the International Search Report (Form PCT/ISA/210) and the Written Opinion of the International Searching Authority (Form PCT/ISA/237) dated May 7, 2019, by the Japanese Patent Office in corresponding International Application No. PCT/JP2019/012383. (8 pages).

International Search Report (PCT/ISA/210) and translation and Written Opinion (PCT/ISA/237) dated May 7, 2019, by the Japanese Patent Office as the International Searching Authority for International Application No. PCT/JP2019/012383.

Office Action (The First Office Action) dated Apr. 20, 2023, by the National Intellectual Property Administration, P. R. China in corresponding Chinese Patent Application No. 201980022826.9 and an English translation of the Office Action. (14 pages).

Office Action (Notice of Reasons for Refusal) dated Mar. 27, 2023, by the Japan Patent Office in corresponding Japanese Patent Application No. 2020-510040 and an English Translation of the Office Action. (5 pages).

* cited by examiner

MEDICAL DEVICE AND TREATMENT METHOD

CROSS-REFERENCES TO RELATED APPLICATIONS

This application is a continuation of International Application No. PCT/JP2019/012383 filed on Mar. 25, 2019, which claims priority to Japanese Application No. 2018-064006 filed on Mar. 29, 2018, the entire content of both of which is incorporated herein by reference.

FIELD

The present disclosure generally relates to a medical device including a maintenance treatment element configured to apply energy to a biological tissue, and a treatment method configured to apply energy to a biological tissue.

BACKGROUND DISCUSSION

Chronic heart failure is a known heart disease. Chronic heart failure is broadly classified into a systolic heart failure and a diastolic heart failure, based on a cardiac function index. In a patient suffering from a diastolic heart failure, myocardial hypertrophy appears, and stiffness (hardness) increases. Consequently, blood pressure increases in a left atrium, and a cardiac pumping function is degraded. In this manner, the patient may show heart failure symptoms such as a pulmonary edema. In addition, another heart disease of a patient who shows the following heart failure symptom where due to pulmonary hypertension, blood pressure increases on a right atrium side, and the cardiac pumping function is degraded.

In recent years, a shunt treatment has attracted attention. For the patients who suffer from the heart failure, a shunt (through-hole) serving as an escape route for increased atrial pressure is formed in an atrial septum, thereby enabling heart failure symptom to be alleviated. In the shunt treatment, the atrial septum is accessed using an intravenous approaching method, and the through-hole is formed having a desired size. For example, a medical device as disclosed in U.S. Pat. No. 8,882,697 may be used for performing the shunt treatment on the atrial septum.

According to the medical device disclosed in U.S. Pat. No. 8,882,697, a shunt hole is enlarged using a balloon serving as an expansion body disposed in a distal portion of a shaft portion, and the shunt hole is maintained by an electrode disposed in the balloon. However, the medical device as disclosed in U.S. Pat. No. 8,882,697 cannot enlarge the shunt hole in a state where a maintenance treatment element such as the electrode is fixed to a biological tissue. Therefore, when the shunt hole is enlarged, there is a possibility that positional displacement may occur between the maintenance treatment element and the biological tissue. For this reason, a therapeutic effect may be reduced by this method.

SUMMARY

A medical device and a treatment method are disclosed, in which energy is accurately applied to a target site by suppressing positional displacement between an expansion body and a biological tissue.

A medical device is disclosed, which includes an elongated shaft portion, and an expansion body disposed in a distal portion of the shaft portion, and configured to expand and contract in a radial direction. The expansion body has a holding portion having a proximal side holding portion and a distal side holding portion which holds a biological tissue, and a movable portion which opens and closes the holding portion.

A treatment method is disclosed of enlarging a through-hole of a biological tissue by using a medical device having an expansion body configured to expand and contract in a radial direction. The treatment method includes positioning a holding portion of the expansion body in the through-hole of the biological tissue, causing the holding portion to hold the biological tissue from both sides of the through-hole, enlarging a diameter of the through-hole by expanding the expansion body, and performing a maintenance treatment by using a maintenance treatment element of the holding portion.

In accordance with an aspect, a medical device is disclosed comprising: an elongated shaft portion; an expansion body disposed in a distal portion of the shaft portion, the expansion body including a plurality of wires in a circumferential direction, each of the plurality of wires configured to expand and contract in a radial direction; each of the plurality of wires comprising: a proximal side expansion portion extending radially in a distal direction from a proximal portion of the expansion body; and a recessed portion disposed distal of the proximal side expansion portion and recessed radially inward; the recessed portion of each of the plurality of wires comprising: a proximal side erected portion connected to a distal end of the proximal side expansion portion; a bottom portion disposed innermost of the recessed portion and distal of the proximal side erected portion; and a distal side erected portion disposed distal of the bottom portion; and wherein the expansion body is configured to expand such that the bottom portion moves radially outward, and the proximal side erected portion and the distal side erected portion move closer to each other.

In accordance with another aspect, a treatment method is disclosed for enlarging a through-hole of a biological tissue by using a medical device having an expansion body having a plurality of wires in a circumferential direction, each of the plurality of wires configured to expand and contract in a radial direction, the method comprising: positioning a recessed portion of each of the plurality of wires of the expansion body in the through-hole of the biological tissue; expanding the expansion body in the through-hole and causing a bottom portion of the recessed portion to move radially outward; enlarging a diameter of the through-hole by the bottom portion of the recessed portion expanding radially outward into the biological tissue; and performing a maintenance treatment by using a maintenance treatment element of the bottom portion of the expansion body.

According to the medical device configured as described above, the biological tissue is held from both sides by the holding portion openable and closeable in a holding direction. Therefore, the positional displacement of the expansion body can be suppressed or minimized.

According to the treatment method configured as described above, the maintenance treatment is performed in a state where the biological tissue is held by the holding portion in this way. Therefore, while the positional displacement of the maintenance treatment element is suppressed, the energy can be relatively accurately applied to the target site.

DETAILED DESCRIPTION

Figure 1:
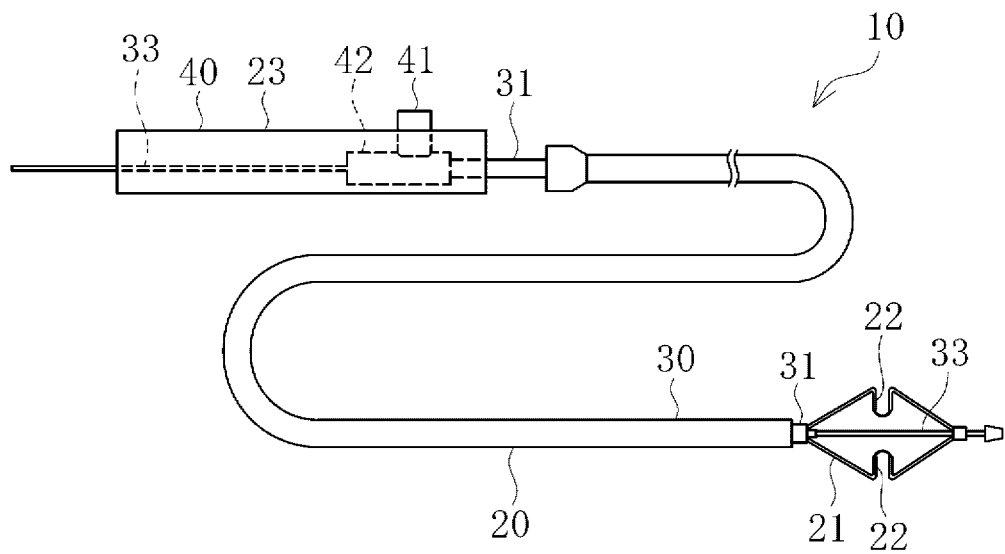
FIG. 1 is a front view illustrating an overall configuration of a medical device according to a first exemplary embodiment.

Set forth below with reference to the accompanying drawings is a detailed description of embodiments of a medical device including a maintenance treatment element configured to apply energy to a biological tissue, and a treatment method configured to apply energy to a biological tissue representing examples of the inventive medical device and treatment method. Note that since embodiments described below are preferred specific examples of the present disclosure, although various technically preferable limitations are given, the scope of the present disclosure is not limited to the embodiments unless otherwise specified in the following descriptions. In some cases, dimensional ratios in the drawings may be exaggerated and different from actual ratios for convenience of description. In addition, in the present disclosure, a side on which a medical device 10 is inserted into a biological lumen will be referred to as a "distal end" or a "distal side", and an operating hand-side will be referred to as a "proximal end" or a "proximal side".

The medical device according to the embodiments described in the disclosure is configured as follows. A through-hole Hh formed in an atrial septum HA of a patient's heart H is enlarged, and further, a maintenance treatment is performed so that the through-hole Hh having an increased diameter is maintained to have an increased size.

Medical Device of First Exemplary Embodiment

As illustrated in FIG. 1, the medical device 10 according to the present embodiment includes an elongated shaft portion 20, an expansion body 21 disposed in a distal portion of the shaft portion 20, and an operation unit 23 disposed in a proximal portion of the shaft portion 20. The expansion body 21 has a maintenance treatment element (energy transfer element) 22 for performing the above-described maintenance treatment.

The shaft portion 20 has an outer shaft 31 that holds the expansion body 21 in the distal portion of the shaft portion 20, and a storage sheath 30 that stores the outer shaft 31. The storage sheath 30 is movable forward to and rearward from the outer shaft 31 in an axial direction. In a state where the storage sheath 30 is moved to the distal side of the shaft portion 20, the storage sheath 30 can internally store the expansion body 21 in a contracted state. In a state where the expansion body 21 is stored, the storage sheath 30 is moved to the proximal side. In this manner, the expansion body 21 can be exposed.

A pulling shaft 33 is stored inside the outer shaft 31. The pulling shaft 33 projects from the distal end to the distal side of the outer shaft 31, and a distal portion of the pulling shaft 33 is fixed to a distal member 35. A proximal portion of the pulling shaft 33 is drawn out (i.e., extends) to the proximal side of the operation unit 23. The distal member 35 to which the distal portion of the pulling shaft 33 is fixed may not be fixed to the expansion body 21. In this manner, the distal member 35 can pull the expansion body 21 in a contracting direction. In addition, when the expansion body 21 is stored in the storage sheath 30, the distal member 35 is separated to the distal side from the expansion body 21. Accordingly, the expansion body 21 can be rather easily moved in an extending direction, and storage capability can be improved.

The operation unit 23 has a housing 40 gripped by an operator, an operation dial 41 that can be rotationally operated by the operator, and a conversion mechanism 42 operated in conjunction with the rotation of the operation dial 41. The pulling shaft 33 is held inside the operation unit 23 by the conversion mechanism 42. In conjunction with the rotation of the operation dial 41, the conversion mechanism 42 can move the held pulling shaft 33 forward and backward along the axial direction. For example, a rack and pinion mechanism can be used as the conversion mechanism 42.

Figure 2:
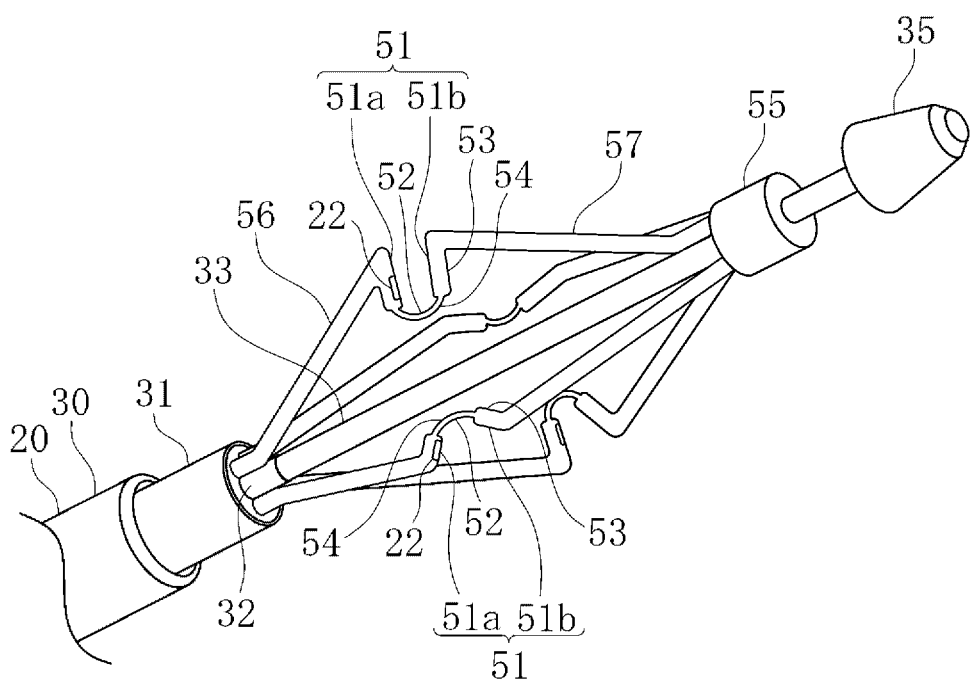
FIG. 2 is an enlarged perspective view illustrating the vicinity of an expansion body.

The expansion body 21 will be described in more detail. As illustrated in FIG. 2, the expansion body 21 has a plurality of wires in a circumferential direction. In the present embodiment, four wires of the expansion body 21 are disposed in the circumferential direction, and each of the four wires is configured to expand and contract in a radial direction. The wire of the expansion body 21 has a proximal side expansion portion 56 extending in a diameter increasing direction from the proximal portion toward the distal side, and a distal side expansion portion 57 extending in the diameter increasing direction from the distal portion toward the proximal side. A proximal side holding portion 51a is disposed in the distal portion of the proximal side expansion portion 56, and a distal side holding portion 51b is disposed in the proximal portion of the distal side expansion portion 57, respectively. The proximal side holding portion 51a and the distal side holding portion 51b form a holding portion 51 that can hold a biological tissue. The proximal portion of the proximal side expansion portion 56 is fixed to the distal portion of the outer shaft 31. A distal portion 55 of the distal side expansion portion 57 is located on the proximal side from the distal member 35 as the expansion body 21 itself expands.

Figure 3:
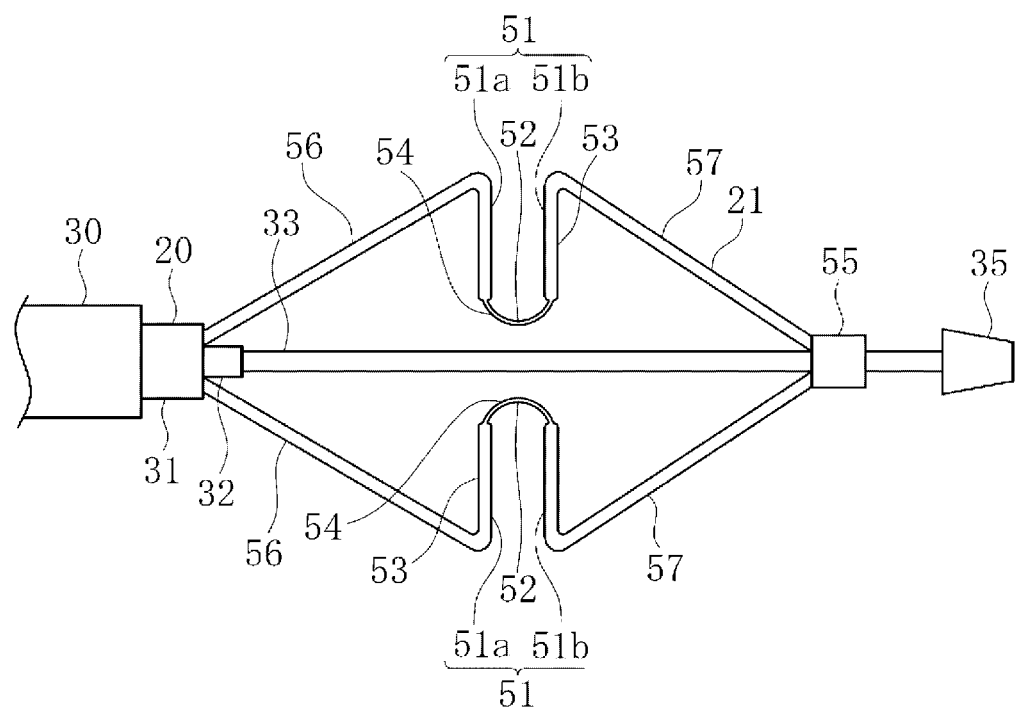
FIG. 3 is an enlarged front view illustrating the vicinity of the expansion body.

As illustrated in FIG. 3, in a central portion of the expansion body 21 in the axial direction, a recessed portion 53 is formed by the proximal side holding portion 51a and the distal side holding portion 51b which face each other in the axial direction, and a movable portion 52 that links the proximal side holding portion 51a and the distal side holding portion 51b with each other. The movable portion 52 has a bending portion 54 having a smaller diameter than that of the holding portion 51. The bending portion 54 has the smaller diameter than that of the holding portion 51. Accordingly, bending portion 54 has bending strength weaker (i.e., less) than that of the holding portion 51. Therefore, the bending portion 54 is likely to be bent when the expansion body 21 expands, and can open and close the holding portion 51 in a fan shape.

For example, the wire forming the expansion body 21 has a flat plate shape cut out from a cylinder. The wire forming the expansion body 21 can have, for example, a thickness of 50 μm to 500 μm and a width of 0.3 mm to 2.0 mm. However, the wire may have a dimension outside this range. In addition, the wire may have a circular shape in a cross section, or may have other shapes in a cross section.

In accordance with an embodiment, a maintenance treatment element 22 is disposed in the proximal side holding portion 51a. When the holding portion 51 grips the atrial septum HA, the proximal side holding portion 51a is located on a right atrium side. Therefore, energy from the maintenance treatment element 22 may be transferred to the atrial septum HA from the right atrium side. However, the maintenance treatment element 22 may be disposed in the distal side holding portion 51b, or may be disposed in both the proximal side holding portion 51a and the distal side holding portion 51b. In accordance with an embodiment, it is desirable that the maintenance treatment element 22 is disposed in a projection portion projecting from a surface of the holding portion 51.

For example, the maintenance treatment element 22 is configured to include a bipolar electrode that receives electric energy from an energy supply device (not illustrated) serving as an external device. In this case, electricity is supplied to the maintenance treatment element 22 disposed in the holding portion 51. The maintenance treatment element 22 and the energy supply device are connected to each other by a conducting wire (not illustrated), for example, coated with an insulating coating material. The conducting wire is drawn outward (i.e., extends outward) via the shaft portion 20 and the operation unit 23, and is connected to the energy supply device.

Alternatively, the maintenance treatment element 22 may be configured to serve as a monopolar electrode. In this case, the electricity is supplied from a counter electrode plate prepared outside a body. In addition, the maintenance treatment element 22 may be a heating element (electrode chip) that generates heat by receiving high-frequency electric energy from the energy supply device. Furthermore, the maintenance treatment element 22 can be configured to include an energy transfer element that applies energy to the through-hole Hh, such as a heater including an electric wire which provides heating and cooling operation or generating frictional heat by using microwave energy, ultrasound energy, coherent light such as laser, a heated fluid, a cooled fluid, or a chemical medium. A specific form of the energy transfer element is not particularly limited.

The wire forming the expansion body 21 can be formed of a metal material. For example, the metal material forming the expansion body 21 may be a titanium-based (Ti—Ni, Ti—Pd, or Ti—Nb—Sn) alloy, a copper-based alloy, stainless steel, β-titanium steel, or a Co—Cr alloy. An alloy having a spring property, for example, a nickel titanium alloy may be used. However, a material of the expansion body 21 is not limited to the materials listed, and the expansion body 21 may be formed of other materials.

The shaft portion 20 has an inner shaft 32 inside the outer shaft 31, and the pulling shaft 33 is stored inside the inner shaft 32. A guide wire lumen is formed in the pulling shaft 33 and the distal member 35 along the axial direction, and a guide wire 11 can be inserted into the guide wire lumen.

In accordance with an exemplary embodiment, it can be preferable that the storage sheath 30, the outer shaft 31, and the inner shaft 32 of the shaft portion 20 are formed of a material having a certain degree of flexibility. For example, the material of the storage sheath 30, the outer shaft 31, and the inner shaft can include polyolefin such as polyethylene, polypropylene, polybutene, ethylene-propylene copolymer, ethylene-vinyl acetate copolymer, ionomer, and a mixture of the above-described two or more materials, fluororesin such as soft polyvinyl chloride resin, polyamide, polyamide elastomer, polyester, polyester elastomer, polyurethane, and polytetrafluoroethylene, polyimide, PEEK, silicone rubber, or latex rubber.

For example, the pulling shaft 33 can be formed from an elongated wire formed of a super elastic alloy such as a nickel-titanium alloy and a copper-zinc alloy, a metal material such as stainless steel, or a resin material having relatively high rigidity is coated with a resin material such as polyvinyl chloride, polyethylene, polypropylene, and ethylene-propylene copolymer.

For example, the material of the distal member 35 can be a polymer material such as polyolefin, polyvinyl chloride, polyamide, polyamide elastomer, polyurethane, polyurethane elastomer, polyimide, and fluororesin or a mixture of a polymer materials. Alternatively, the distal member 35 can be formed of a multilayer tube containing two or more polymer materials.

Figure 4A:
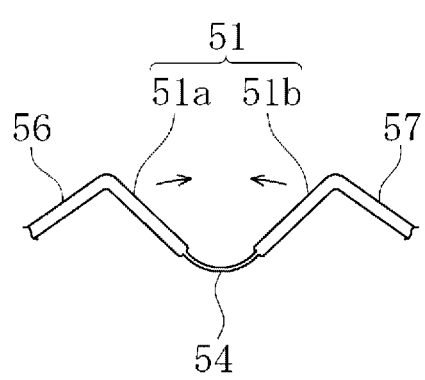
FIGS. 4A and 4B are enlarged front views illustrating an open state and a closed state of a holding portion, respectively.
Figure 4B:
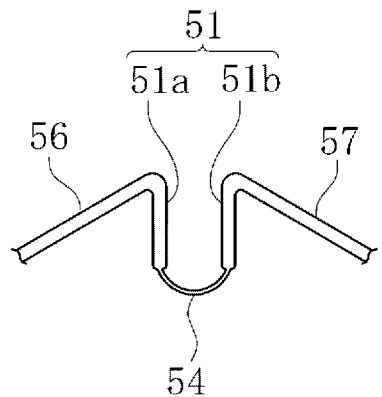

As illustrated in FIG. 3, the expansion body 21 exposed outward of the storage sheath 30 is brought into an expanded state in the radial direction due to a self-expanding force of the expansion body 21. When the expansion body 21 expands, the recessed portion 53 deforms from a state where the holding portion 51 is open in a fan shape (FIG. 4A) to a state where the bending portion 54 is bent and the holding portion 51 is closed in the holding direction (FIG. 4B). The storage sheath 30 that stores the expansion body 21 in a contracted state is a restriction element which maintains an open state of the holding portion 51. The restriction element is released, that is, the expansion body 21 is exposed outward of the storage sheath 30. In this manner, the holding portion 51 can be closed in the holding direction. As will be described later, the expansion body 21 expands in a state where the recessed portion 53 is positioned in the atrial septum HA. Therefore, since the holding portion 51 is closed in the axial direction, the atrial septum HA can be held from both sides.

Figure 5:
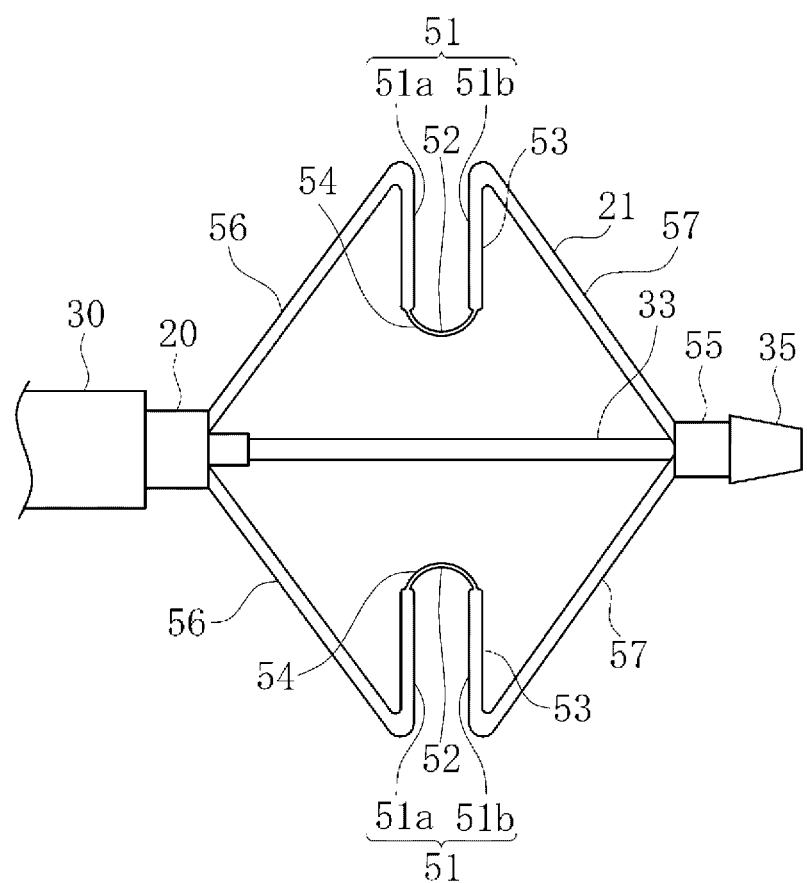
FIG. 5 is an enlarged front view illustrating the vicinity of the expansion body having an increased diameter.

As illustrated in FIG. 5, the pulling shaft 33 is moved to the proximal side so that the distal member 35 moves to the proximal side. In this manner, the distal portion 55 of the expansion body 21 is moved to the proximal side. In response to the movement, the expansion body 21 further expands in the radial direction. The pulling shaft 33 is moved to the distal side. Accordingly, from this state, the expansion body 21 can return to a state illustrated in FIG. 3.

Treatment Method Using Medical Device of First Exemplary Embodiment

Figure 7:
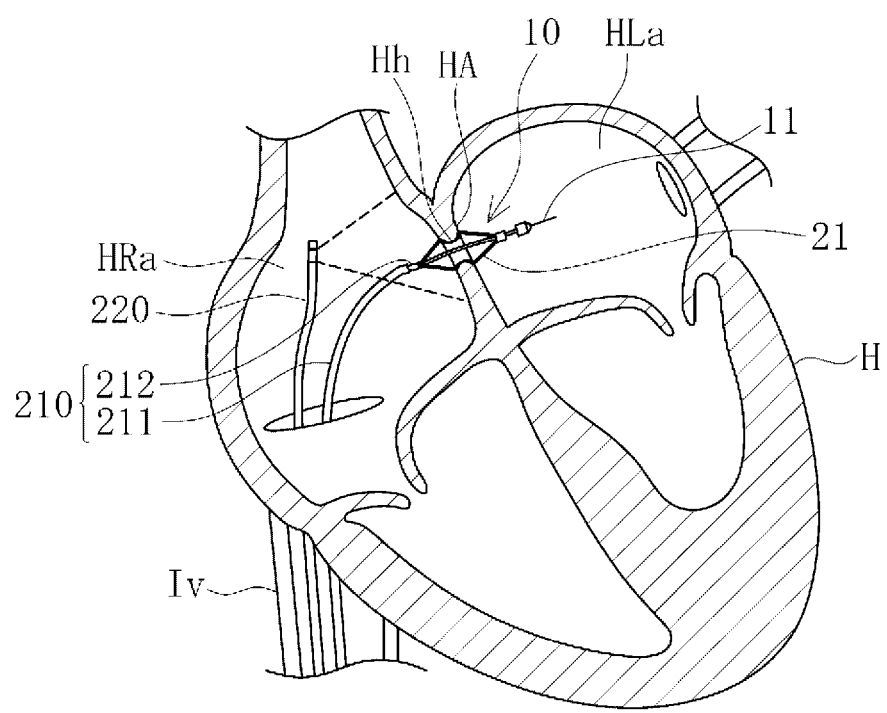
FIG. 7 is a view for describing the treatment method according to the present embodiment, and is a view for schematically describing a state where the expansion body is disposed in a through-hole of an atrial septum, in which a biological tissue is illustrated in a sectional view and the medical device is illustrated in a front view, respectively.

A treatment method using the medical device 10 will be described. As an example, the treatment method according to the present embodiment is performed on a patient suffering from heart failure (left heart failure). More specifically, as illustrated in FIG. 7, the treatment method is performed on the patient suffering from a chronic heart failure, who has high blood pressure in a left atrium HLa due to myocardial hypertrophy appearing in a left ventricle of the heart H and increased stiffness (hardness).

Figure 6:
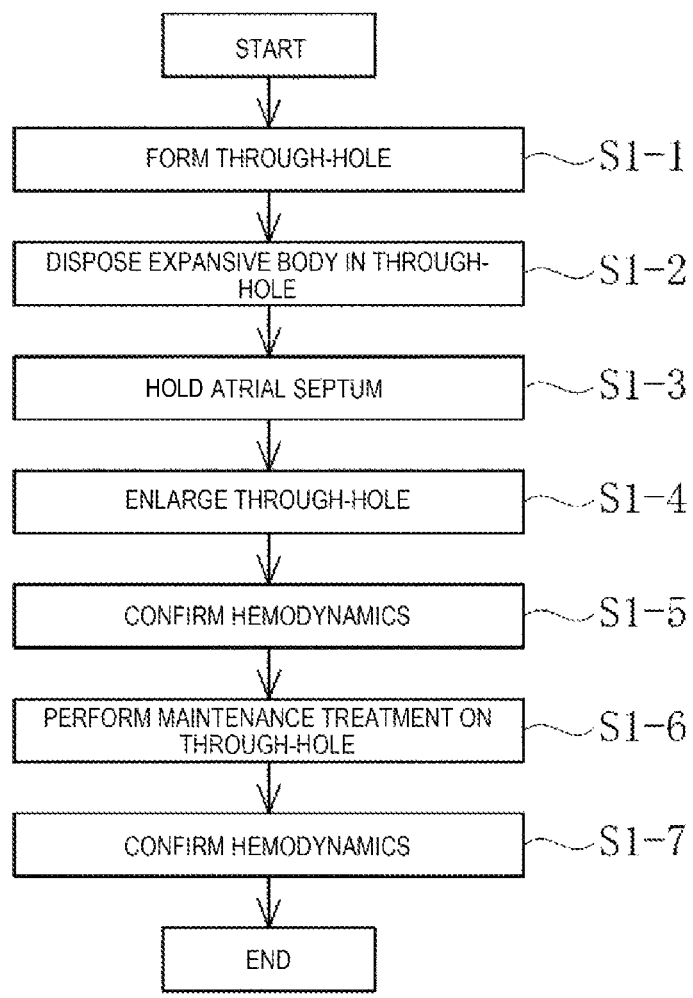
FIG. 6 is a flowchart of a treatment method using the medical device.

As illustrated in FIG. 6, the treatment method according to the present embodiment includes forming the through-hole Hh in the atrial septum HA (S1-1), disposing the expansion body 21 in the through-hole Hh (S1-2), holding the atrial septum HA by using the expansion body 21 (S1-3), enlarging the diameter of the through-hole Hh by using the expansion body 21 (S1-4), confirming hemodynamics in the vicinity of the through-hole Hh (S1-5), performing the maintenance treatment for maintaining the size of the through-hole Hh (S1-6), and confirming the hemodynamics in the vicinity of the through-hole Hh after the maintenance treatment is performed (S1-7).

When the through-hole Hh is formed, an operator delivers an introducer 210 in which a guiding sheath 211 and a dilator 212 are combined with each other, to the vicinity of the atrial septum HA. For example, the introducer 210 can be delivered to a right atrium HRa via an inferior vena cava Iv. In addition, the introducer 210 can be delivered using the guide wire 11. The operator can insert the guide wire 11 into the dilator 212, and can deliver the introducer 210 along the guide wire 11. The introducer 210 and the guide wire 11 can be inserted into a living body by using a known method such as using a blood vessel introducer.

Figure 8:
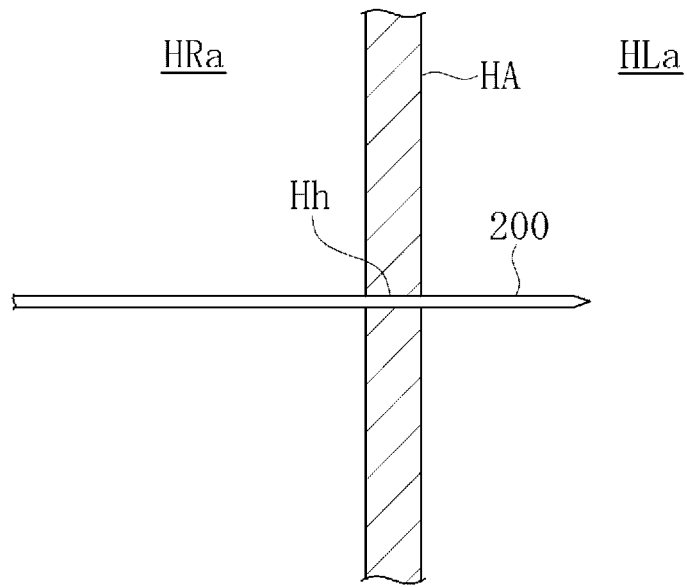
FIG. 8 is a view for schematically describing a state where a puncture device punctures the atrial septum, in which the biological tissue is illustrated in a sectional view and the medical device is illustrated in a front view, respectively.

As illustrated in FIG. 8, in the forming of the through-hole Hh in the atrial septum HA (S1-1), the operator causes a puncture device 200 to penetrate from the right atrium HRa side toward the left atrium HLa side, thereby forming the through-hole Hh. For example, a device such as a wire having a sharp distal end can be used as the puncture device 200. The puncture device 200 is inserted into the dilator 212, and is delivered to the atrial septum HA. The puncture device 200 can be delivered to the atrial septum HA instead of the guide wire 11 after the guide wire 11 is removed from the dilator 212.

Figure 9:
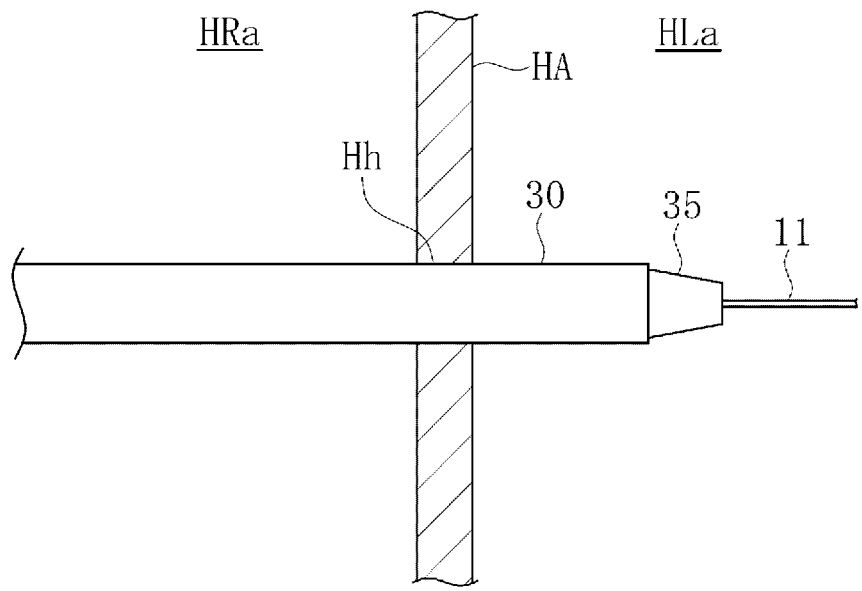
FIG. 9 is a view for schematically describing a state where a storage sheath is inserted into the atrial septum, in which the biological tissue is illustrated in a sectional view and the medical device is illustrated in a front view, respectively.

In the disposing of the expansion body 21 in the through-hole Hh (S1-2), as illustrated in FIG. 9, the medical device 10 is first delivered to the vicinity of the atrial septum HA along the guide wire 11, and wherein the guide wire 11 has been inserted in advance of the medical device 10. At this time, the distal portion of the medical device 10 penetrates the atrial septum HA, and reaches the left atrium HLa. In addition, when the medical device 10 is inserted, the expansion body 21 is in a state of being stored in the storage sheath 30.

Figure 10:
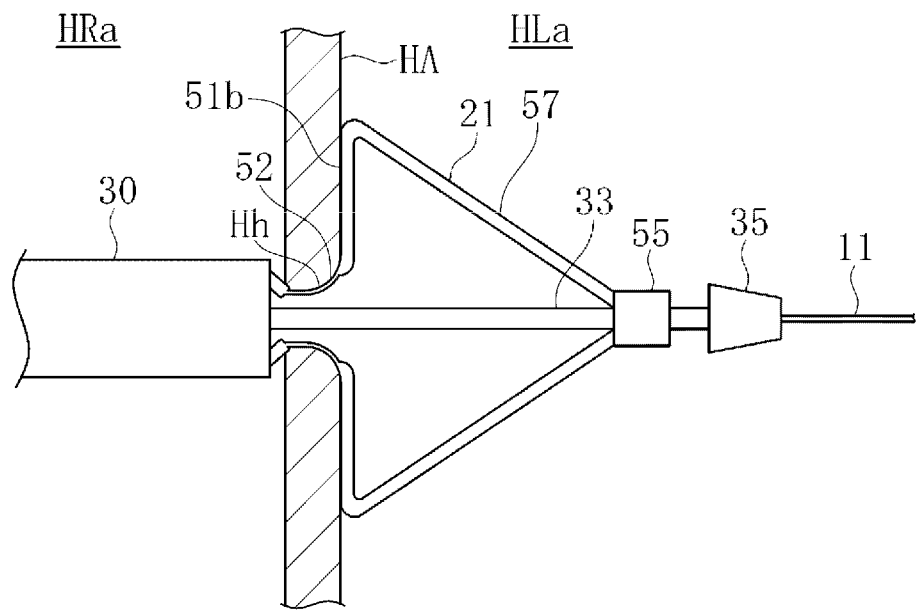
FIG. 10 is a view for schematically describing a state where a distal side of the expansion body is exposed from the storage sheath, in which the biological tissue is illustrated in a sectional view and the medical device is illustrated in a front view, respectively.

Next, as illustrated in FIG. 10, the expansion body 21 is moved to the distal side so that the distal side portion of the expansion body 21 is exposed inside the left atrium HLa. In this manner, the distal side expansion portion 57 in the expansion body 21 expands in the radial direction. Here, the distal side holding portion 51b of the expansion body 21 is pressed against a surface on the left atrium HLa side of the atrial septum HA. In this manner, the expansion body 21 is positioned.

Figure 11:
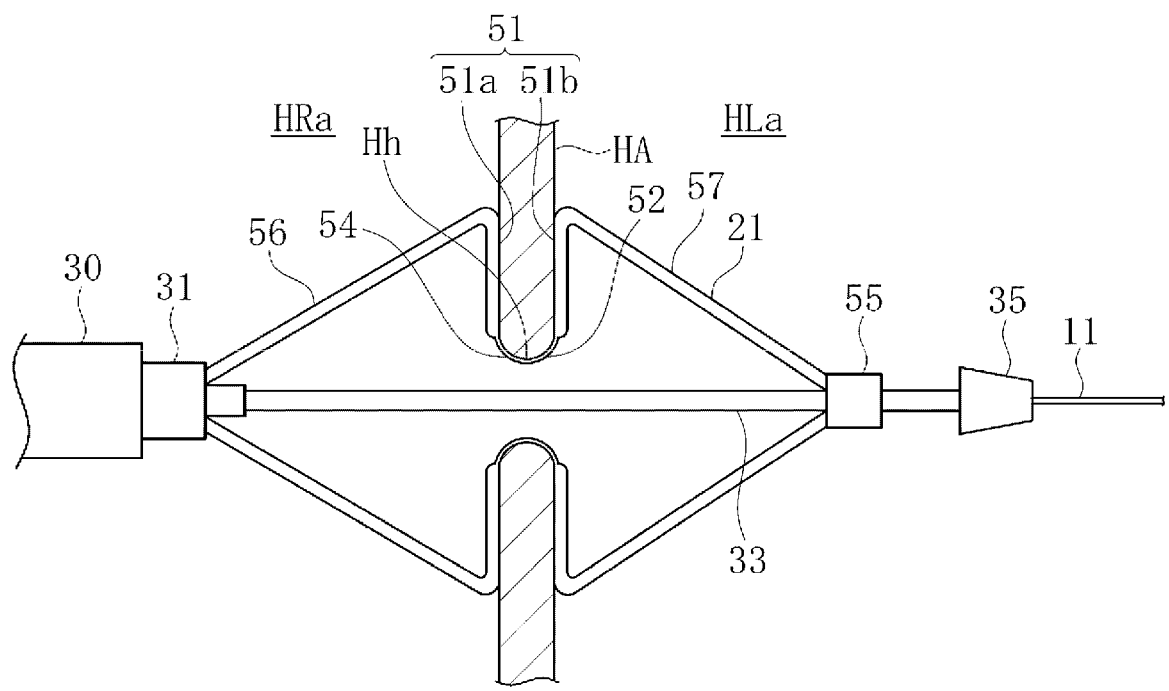
FIG. 11 is a view for schematically describing a state where the whole expansion body is exposed from the storage sheath and the atrial septum is held, in which the biological tissue is illustrated in a sectional view and the medical device is illustrated in a front view, respectively.

Next, as illustrated in FIG. 11, the storage sheath 30 is moved to the proximal side so that the whole or entirety of the expansion body 21 is exposed. In the manner, the proximal side expansion portion 56 in the expansion body 21 expands in the radial direction inside the right atrium HRa. At this time, as described above, in the recessed portion 53, the movable portion 52 is bent and deformed by the bending portion 54. The proximal side holding portion 51a and the distal side holding portion 51b grip the atrial septum HA from both sides. In this manner, the holding of the atrial septum HA using the expansion body 21 (S1-3) is performed. In the holding of the atrial septum HA using the expansion body 21 (S1-3), the movable portion 52 does not expand to be larger than an outer diameter of the storage sheath 30, and does not substantially enlarge the through-hole Hh. That is, in the holding of the atrial septum HA using the expansion body 21 (S1-3), the distal side expansion portion 57 and the proximal side expansion portion 56 in the expansion body 21 expand in the radial direction, and the expansion body 21 in which the movable portion 52 does not substantially expand in the radial direction expands primarily. In this manner, the atrial septum HA may be held by the holding portion 51.

Figure 12:
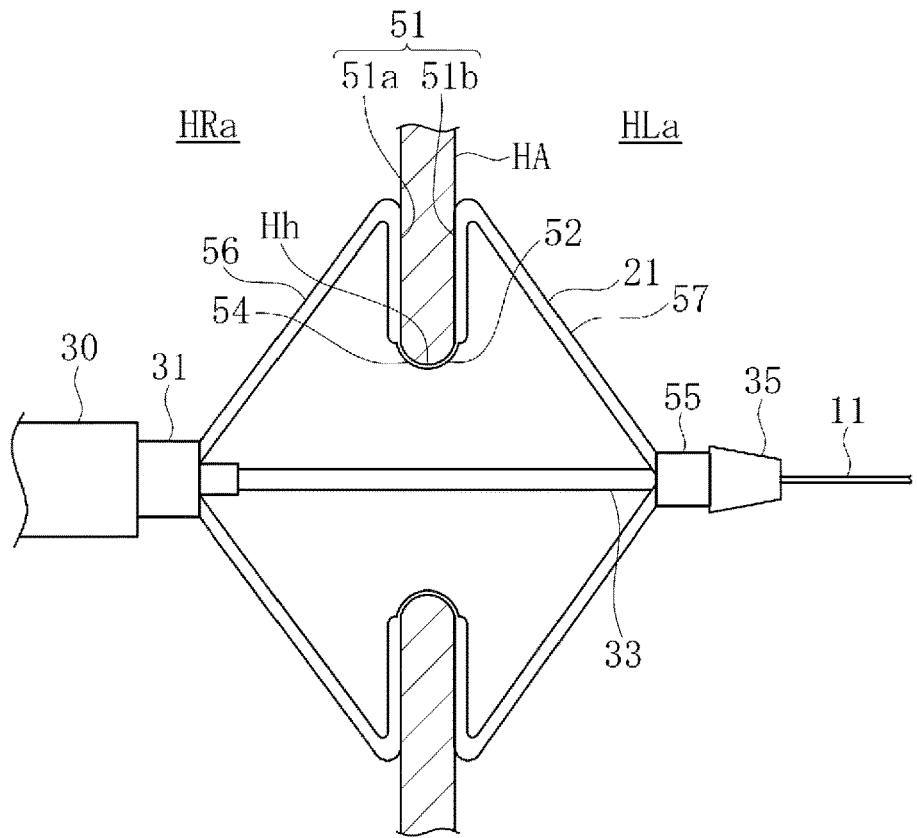
FIG. 12 is a view for schematically describing a state where the through-hole of the atrial septum is enlarged by increasing the diameter of the expansion body, in which the biological tissue is illustrated in a sectional view and the medical device is illustrated in a front view, respectively.

In the enlarging of the diameter of the through-hole Hh by using the expansion body 21 (S1-4), as illustrated in FIG. 12, the operator operates the operation unit 23 in a state where the atrial septum HA is held by the holding portion 51. In this manner, the pulling shaft 33 is moved to the proximal side. The expansion body 21 further expands in the radial direction due to the distal member 35 disposed in the distal portion of the pulling shaft 33. At this time, the proximal side expansion portion 56, the distal side expansion portion 57, and the movable portion 52 of the expansion body 21 all expand in the radial direction. Since the expansion body 21 expands secondarily, the held through-hole Hh is widened in the radial direction. In this way, an expanding operation is performed in the radial direction in a state where the atrial septum HA is held by the holding portion 51 from both sides. Accordingly, the diameter of the through-hole Hh of the atrial septum HA can be effectively enlarged.

After the through-hole Hh is enlarged, the hemodynamics is confirmed in the vicinity of the through-hole Hh (S1-5). As illustrated in FIG. 7, the operator delivers a hemodynamics confirming device 220 to the right atrium HRa by way of the inferior vena cava Iv. For example, a known echo catheter can be used as the hemodynamics confirming device 220. The operator can display an echo image acquired by the hemodynamics confirming device 220 on a display apparatus such as a display, and can confirm a blood volume passing through the through-hole Hh, based on a result of the echo image.

In addition, the hemodynamics can be confirmed by measuring pressure of each portion. The pressure can be measured on the left atrium side through the guide wire lumen of the shaft portion 20. Simultaneously, the pressure can be measured on the right atrium side through a gap between the storage sheath 30 and the outer shaft 31. The pressure can be measured by connecting a known pressure measurement device to the shaft portion 20. In this way, the pressure is measured. Accordingly, it is possible to confirm that the pressure in the left atrium is lowered, and that the pressure in the right atrium is not excessively risen (i.e., excessively higher). In this manner, a therapeutic effect of the shunt treatment can be improved, and a risk of excessively enlarging the through-hole Hh can be reduced.

Next, the operator performs the maintenance treatment for maintaining the size of the through-hole Hh (S1-6). In the maintenance treatment, high-frequency energy is applied to an edge portion of the through-hole Hh through the maintenance treatment element 22, thereby cauterizing (heating and cauterizing) the edge portion of the through-hole Hh by using the high-frequency energy. When the biological tissue in the vicinity of the edge portion of the through-hole Hh is cauterized through the maintenance treatment element 22, a degenerated portion having the degenerated biological tissue may be formed in the vicinity of the edge portion. The biological tissue in the degenerated portion is in a state where elasticity is lost. Accordingly, the through-hole Hh can maintain a shape widened by the expansion body 21.

In a state where the holding portion 51 having the maintenance treatment element 22 holds the atrial septum HA as described above, the maintenance treatment is performed. Therefore, when the maintenance treatment is performed, the positional displacement of the maintenance treatment element 22 can be prevented. In addition, a difference in bending strength is adjusted between the holding portion 51 and the movable portion 52. In this manner, a pressing force and a contact area of the maintenance treatment element 22 can be controlled with respect to the biological tissue. In this manner, fluctuations in cauterizing can be minimized, and reliable maintenance treatment can be performed.

The maintenance treatment element 22 is disposed in the projection portion of the holding portion 51. Therefore, the holding portion 51 is pressed against the atrial septum HA. In this manner, the maintenance treatment is performed in a state where the maintenance treatment element 22 is incorporated in the biological tissue. In this manner, the maintenance treatment element 22 can be prevented from coming into contact with the blood during the maintenance treatment. Accordingly, it is possible to suppress appearance of a thrombus caused by a current leaking into the blood.

After the maintenance treatment is performed, the hemodynamics are confirmed again in the vicinity of the through-hole Hh (S1-7). In a case where the blood volume passing through the through-hole Hh reaches a desired volume, the operator decreases the diameter of the expansion body 21. After the expansion body 21 is stored in the storage sheath 30, the expansion body 21 is removed from the through-hole Hh. Furthermore, the whole medical device 10 is removed outward of the living body, and the treatment is completed.

Medical Device of Second Exemplary Embodiment

Figure 13:
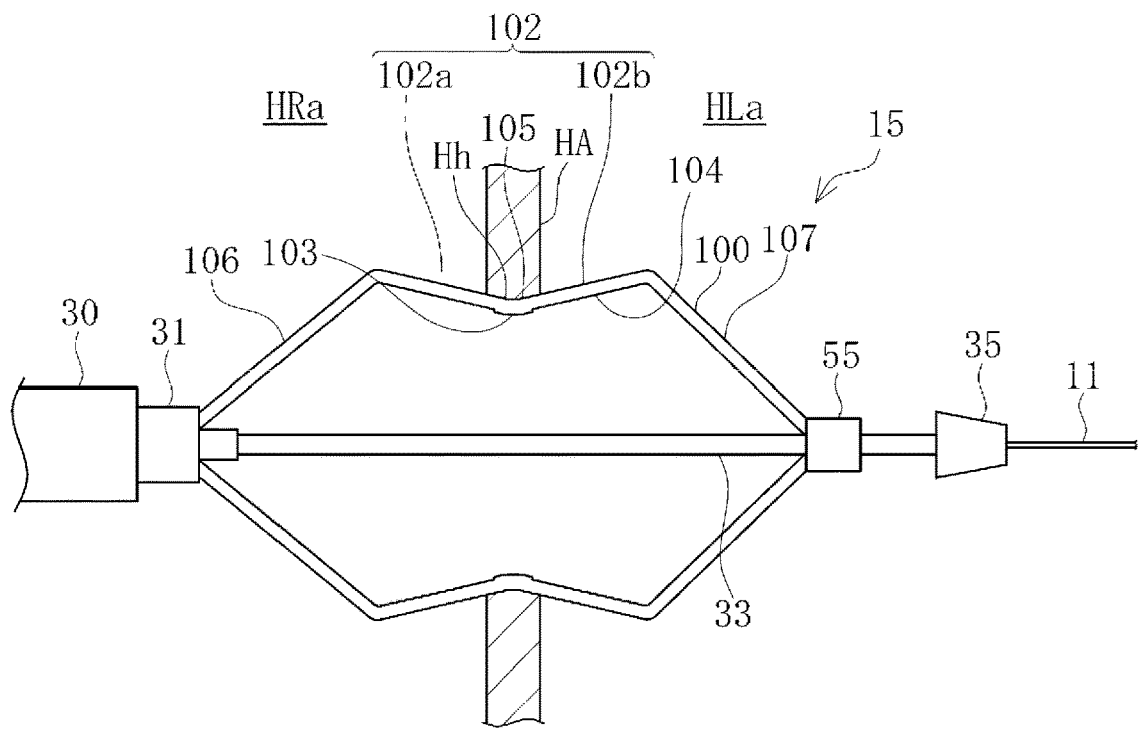
FIG. 13 is a view for schematically describing a state where the through-hole of the atrial septum is enlarged by an expansion body of a medical device according to a second embodiment, in which the biological tissue is illustrated in a sectional view and the medical device is illustrated in a front view, respectively.

Next, a medical device 15 according to a second exemplary embodiment will be described. The medical device 15 according to the second exemplary embodiment is the same as that according to the first exemplary embodiment except for a configuration of an expansion body 100, and common elements will be omitted in the description. As illustrated in FIG. 13, the expansion body 100 has a plurality of wires in the circumferential direction, and each of the plurality of wires has a proximal side expansion portion 106, a distal side expansion portion 107, and a movable portion 103. Each of the plurality of wires of the expansion body 100 has a recessed portion 104 in a central portion in the axial direction. The recessed portion 104 is formed by a holding portion 102 having the proximal side holding portion 102a and the distal side holding portion 102b, and the movable portion 103 disposed between the holding portions 102. For example, the movable portion 103 has a bending portion 105 which has a larger diameter than that of the holding portion 102 and which has greater bending strength than that of the holding portion 102. Therefore, the expansion body 100 has a shape so that the holding portion 102 is largely opened and the movable portion 103 is separated from the pulling shaft 33 in an outer diameter direction of the storage sheath 30.

Figure 14:
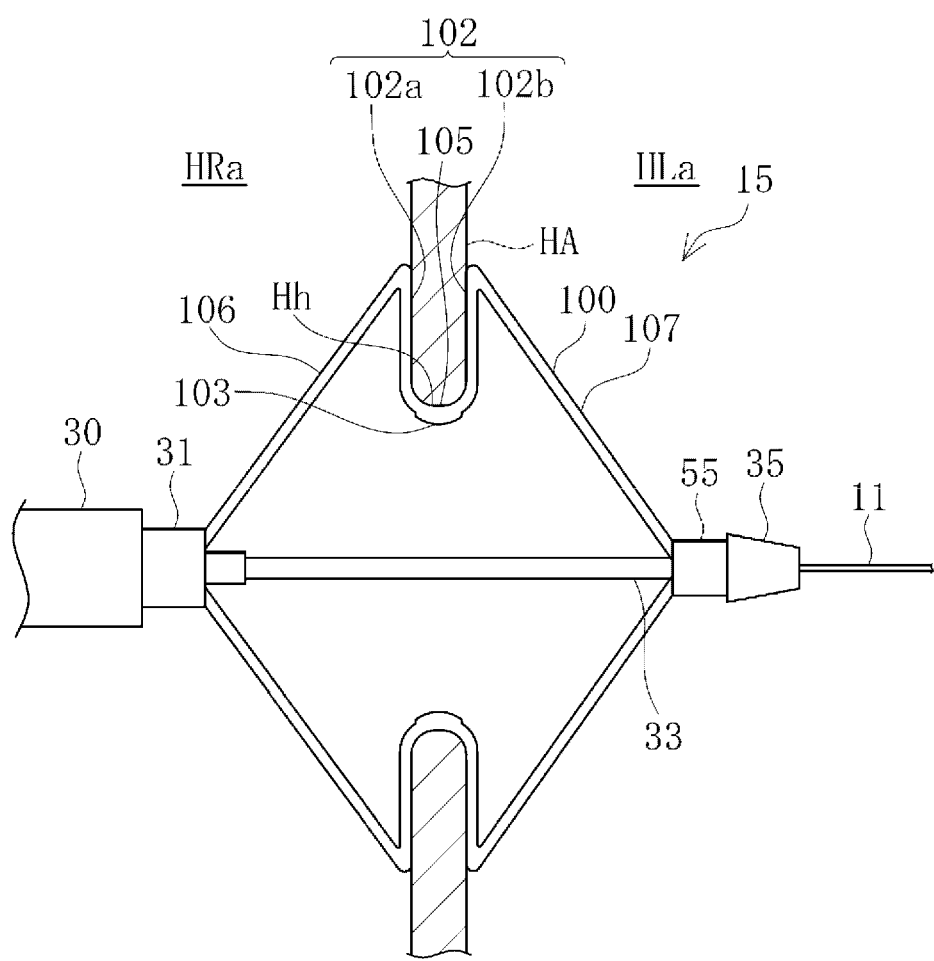
FIG. 14 is a view for schematically describing a state where the atrial septum is held by the expansion body of the medical device according to the second embodiment, in which the biological tissue is illustrated in a sectional view and the medical device is illustrated in a front view, respectively.

In accordance with an exemplary embodiment, the bending portion 105 has the bending strength greater than that of the holding portion 102. Accordingly, when the expansion body 100 is exposed from the storage sheath 30 and expands in the radial direction, while the bending portion 105 is not bent much, the expansion body 100 largely expands in the radial direction. In this manner, as illustrated in FIG. 13, in the expansion body 100 disposed in the through-hole Hh of the atrial septum HA, all of the proximal side expansion portion 106, the distal side expansion portion 107, and the movable portion 103 expand in the radial direction, and enlarge the diameter of the through-hole Hh. After the diameter of the through-hole Hh is enlarged, the pulling shaft 33 is moved to the proximal side. In this manner, as illustrated in FIG. 14, the bending portion 105 is bent, and the holding portion 102 is closed in the holding direction to grip the atrial septum HA from both sides.

In this way, in a case where the holding portion 102 is opened and closed by the movable portion 103 in a fan shape, expanding and holding sequences can be changed by changing a balance in the bending strength of the holding portion 102 and the movable portion 103.

In addition, the balance in the bending strength of the holding portion and the movable portion may be adjusted. In this manner, an expanding operation and a holding operation of the expansion body can be simultaneously performed. In this case, the expansion body is caused to expand in the through-hole Hh. Accordingly, while the through-hole Hh is held from both sides, the diameter of the through-hole Hh can be simultaneously enlarged.

Treatment Method Using Medical Device of Second Exemplary Embodiment

Figure 15:
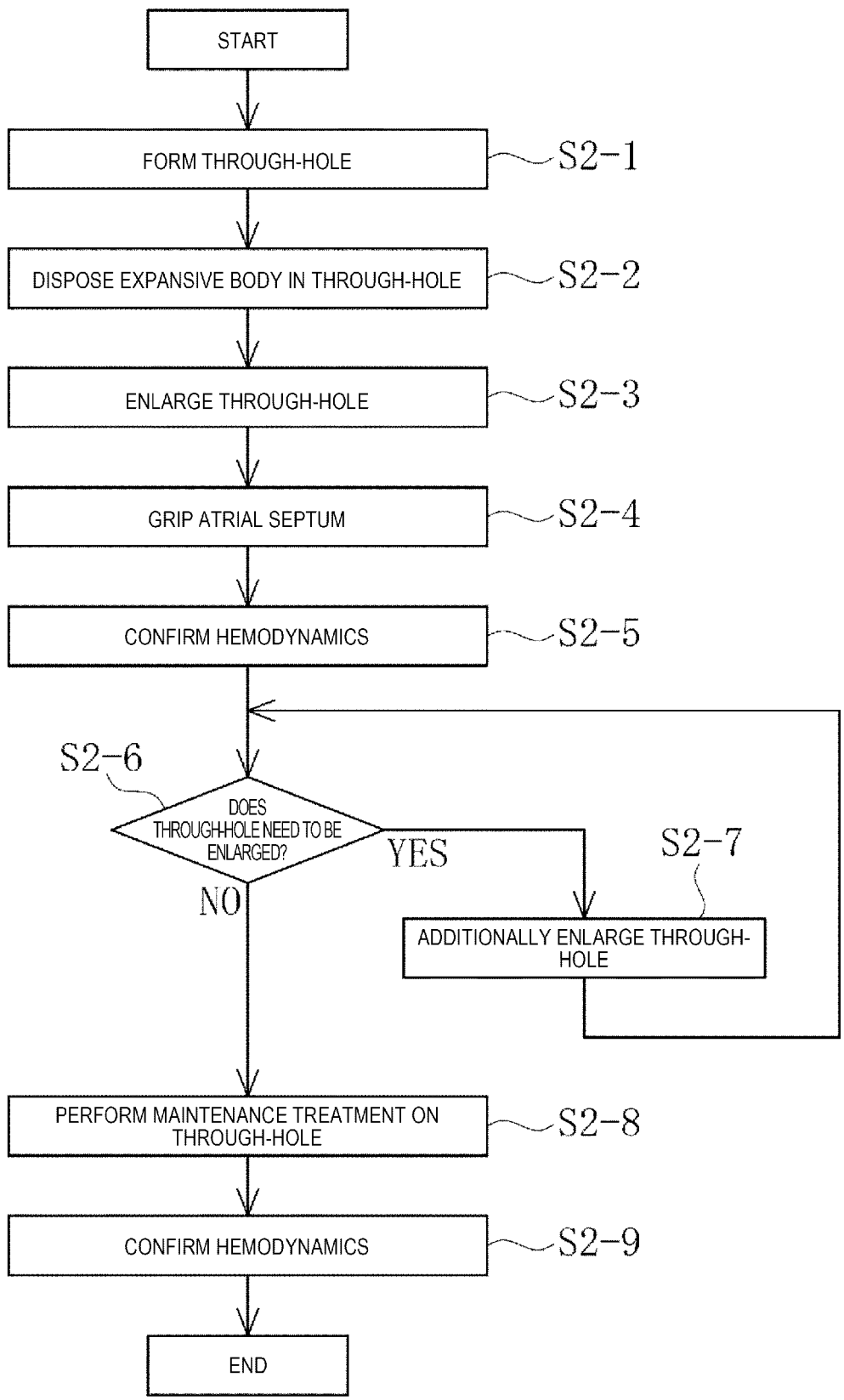
FIG. 15 is a flowchart of a treatment method using the medical device according to the second embodiment.

A treatment method using the medical device 15 according to the second exemplary embodiment will be described. As illustrated in FIG. 15, the treatment method according to the second exemplary embodiment includes forming the through-hole Hh in the atrial septum HA (S2-1), disposing the expansion body 100 in the through-hole Hh (S2-2), enlarging the diameter of the through-hole Hh by using the expansion body 100 (S2-3), and holding the atrial septum HA by using the expansion body 100 (S2-4). Here, S2-1 to S2-2 are the same as S1-1 to S1-2 in the first exemplary embodiment, and thus, description of the forming of the through-hole Hh in the atrial septum HA (S2-1) and the disposing of the expansion body 100 in the through-hole Hh (S2-2) will be omitted.

In addition, the treatment method according to the second exemplary embodiment includes confirming the hemodynamics in the vicinity of the through-hole Hh after S2-4 (S2-5), determining whether the through-hole Hh needs to be additionally enlarged (S2-6), additionally enlarging the through-hole Hh, in a case where it is determined that the through-hole Hh needs to be additionally enlarged in S2-6 (S2-7), performing the maintenance treatment for maintaining the size of the through-hole Hh (S2-8), and confirming the hemodynamics in the vicinity of the through-hole Hh after the maintenance treatment is performed (S2-9). Here, S2-8 to S2-9 are the same as S1-6 to S1-7 in the first embodiment, and thus, description of the performing of the maintenance treatment for maintaining the size of the through-hole Hh (S2-8), and the confirming of the hemodynamics in the vicinity of the through-hole Hh after the maintenance treatment is performed will be omitted.

Until the disposing of the expansion body 100 in the through-hole Hh (S2-2), the expansion body 100 is in a state of being stored inside the storage sheath 30. In the enlarging of the diameter of the through-hole Hh by using the expansion body 100 (S2-3), the operator moves the storage sheath 30 to the proximal side so that the expansion body 100 is exposed from the storage sheath 30. In this manner, as illustrated in FIG. 13, in the expansion body 100, all of the proximal side expansion portion 106, the distal side expansion portion 107, and the movable portion 103 expand in the radial direction, and the diameter of the through-hole Hh is enlarged.

After the diameter of the through-hole Hh is enlarged, in the holding of the atrial septum HA by using the expansion body 100 (S2-4), the operator moves the pulling shaft 33 to the proximal side. In this manner, the bending portion 105 of the movable portion 103 is bent, and the holding portion 102 is closed in the holding direction. In this manner, as illustrated in FIG. 14, the holding portion 102 holds the atrial septum HA from both sides.

In a case where the hemodynamics are confirmed in the vicinity of the through-hole Hh (S2-5) and it is determined that the through-hole Hh needs to be further enlarged, the through-hole Hh is additionally enlarged (S2-7). The through-hole Hh is additionally enlarged by further moving the pulling shaft 33 to the proximal side in a state illustrated in FIG. 14 so that the diameter of the expansion body 100 is increased. In addition, in that state, the pulling shaft 33 is moved to the distal side, the diameter of the expansion body 100 is decreased once. Thereafter, the pulling shaft 33 is moved to the proximal side again. Accordingly, the diameter of the expansion body 100 can be increased. Furthermore, the pulling shaft 33 can be repeatedly moved forward and rearward to widen the through-hole Hh little by little.

In addition, a preliminarily enlarging the through-hole can be performed between the disposing the expansion body 100 in the through-hole Hh (S2-2) and the enlarging of the diameter of the through-hole Hh by using the expansion body 100 (S2-3). The through-hole is preliminarily enlarged in a case where the biological tissue is so hardened that the through-hole cannot be sufficiently enlarged by the expansion force of the expansion body 100. When the through-hole is preliminarily enlarged, as in the enlarging the diameter of the through-hole Hh by using the expansion body 100 (S2-3), the expansion body 100 expands to enlarge the diameter of the through-hole. As in the holding of the atrial septum HA by using the expansion body 100 (S2-4), the pulling shaft 33 is moved to the proximal side. In this manner, the holding portion 102 holds the atrial septum HA from both sides. Furthermore, as in the case where it is determined that the through-hole Hh needs to be additionally enlarged (S2-7), the pulling shaft 33 is further moved to the proximal side. In this manner, the expansion body 100 further expands so that the through-hole Hh is widened. This operation may be performed once or multiple times. Accordingly, the biological tissue around the through-hole Hh is torn, and the through-hole Hh can be subsequently enlarged.

In the present embodiment, after the through-hole Hh of the atrial septum HA is enlarged by the holding portion 102, the through-hole Hh is held by the holding portion 102. However, as described above, the balance in the bending strength of the holding portion 102 and the movable portion 103 may be adjusted. In this manner, in response to the expansion of the expansion body 100, the through-hole Hh may be simultaneously enlarged and held.

Modification Example of Movable Portion

Figure 16A:
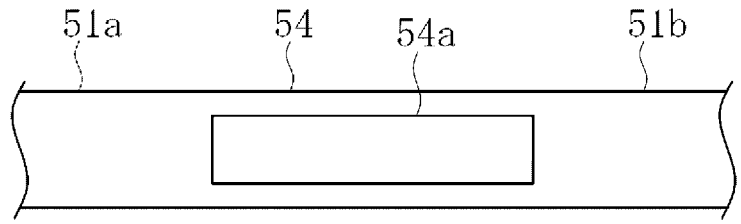
FIGS. 16A-16E are plan views illustrating exemplary embodiments of a movable portion.
Figure 16B:
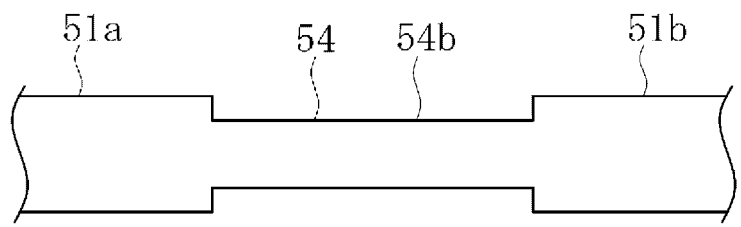
Figure 16C:
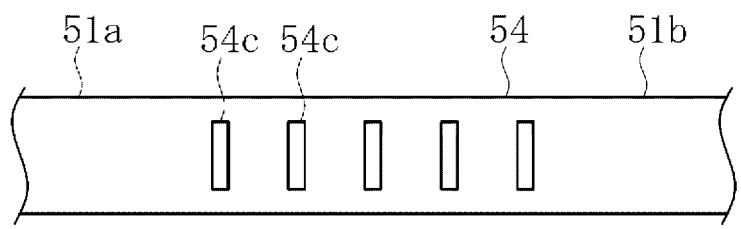
Figure 16D:
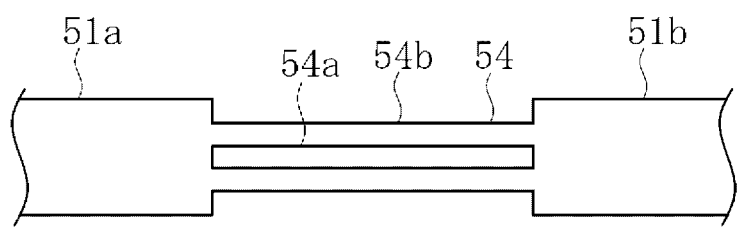
Figure 16E:
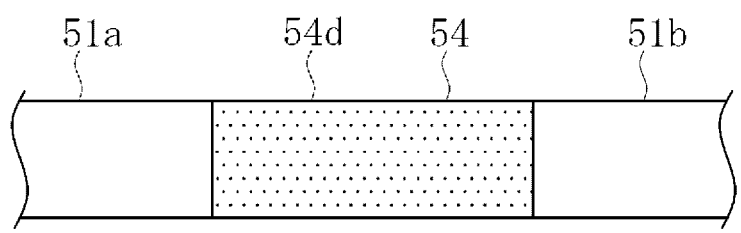

In accordance with an exemplary embodiment, the movable portion that opens and closes the holding portion can have various forms. As a shape for reducing the bending strength in the bending portion 54, the first exemplary embodiment adopts a configuration in which the bending portion 54 has a diameter smaller than that of the holding portion 51. In addition, as illustrated in FIG. 16A, a slit portion 54a can be provided. In addition, as illustrated in FIG. 16B, a cutout portion 54b can be provided. In addition, as illustrated in FIG. 16C, a plurality of small hole portions 54c can be provided. In addition, as illustrated in FIG. 16D, both the slit portion 54a and the cutout portion 54b can be provided. In addition, as illustrated in FIG. 16E, a soft portion 54d formed of a material softer than that of the surroundings can be provided. In addition, the movable portion can be formed by providing a portion thinner than the surroundings.

Figure 17A:
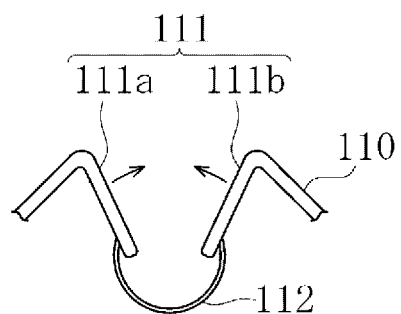
FIGS. 17A and 17B are enlarged front views illustrating another exemplary embodiment of the movable portion.
Figure 17B:
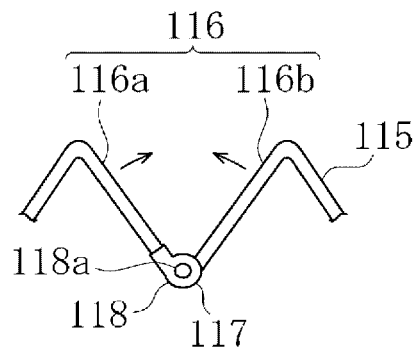

As illustrated in FIG. 17A, a movable portion 112 may link the proximal side holding portion 111a and an intermediate portion in a longitudinal direction of the distal side holding portion 111b with each other. In addition, as illustrated in FIG. 17B, a movable portion 117 may have a hinge portion 118 that enables the proximal side holding portion 116a and the distal side holding portion 116b to pivot relative to each other. The hinge portion 118 has a rotary shaft portion 118a. A biasing force may be applied to the rotating shaft portion 118a in a direction in which the holding portion 116 is closed. In this manner, the atrial septum HA can be elastically held by the holding portion 116.

Figure 18A:
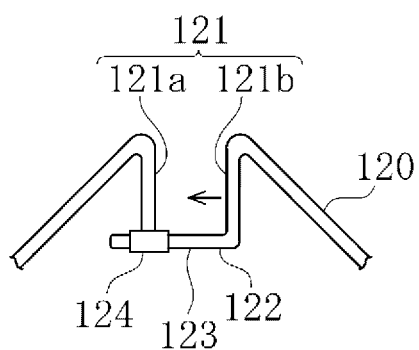
FIGS. 18A-18C are enlarged front views illustrating an example of the movable portion configured to include a parallel movement portion.

The movable portion is not limited to a case where the holding portion is opened and closed in a fan shape, and may cause the holding portion to move in parallel along the axial direction of the shaft portion 20. As illustrated in FIG. 18A, a parallel movement portion 122 can be disposed in the expansion body 120. The parallel movement portion 122 has an extension portion 123 extending from the distal side holding portion 121b to the proximal side holding portion 121a, and the proximal side holding portion 121a has a slide holding portion 124 that holds the extension portion 123. The extension portion 123 can be moved along the axial direction by the slide holding portion 124. In this manner, a distance between the holding portions 121 can be changed, and the holding portions 121 can be opened and closed in the holding direction. For example, the extension portion 123 can be slid using a wire (not illustrated) linked with the extension portion 123 and extending to a hand-side portion.

Figure 18B:
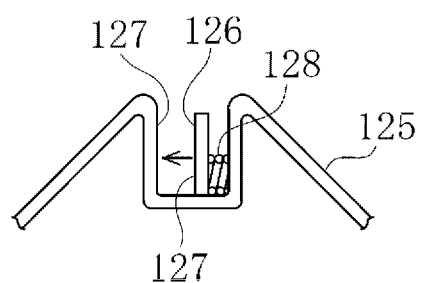

As illustrated in FIG. 18B, the parallel movement portion 126 can have a structure in which one holding portion 127 is supported by an elastic body 128, for example, a spring. In this manner, the holding portion 127 supported by the elastic body 128 is movable along the axial direction. In this case, the elastic body 128 biases the holding portion 127 in an extension direction. The biasing force can be restricted using a wire (not illustrated) linked with the holding portion 127 or the elastic body 128 and extending to the hand-side portion. In addition, a lock portion (not illustrated) for restricting the biasing force of the elastic body 128 may be disposed in the expansion body 125 in a contracted state, and the lock portion may be released as the expansion body 125 expands in the radial direction.

Figure 18C:
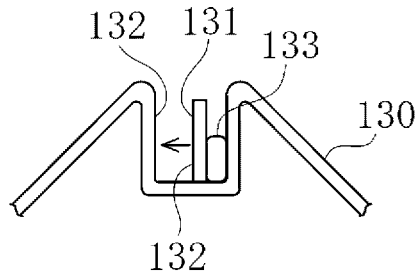

As illustrated in FIG. 18C, the parallel movement portion 131 can have a structure in which one holding portion 132 is supported by a moving balloon 133. As the moving balloon 133 is inflated and deflated, the holding portion 132 can move along the axial direction. In this case, an additional lumen (not illustrated) for supplying an inflating fluid to the moving balloon 133 is provided.

Modification Example of Expansion Body

Figure 19:
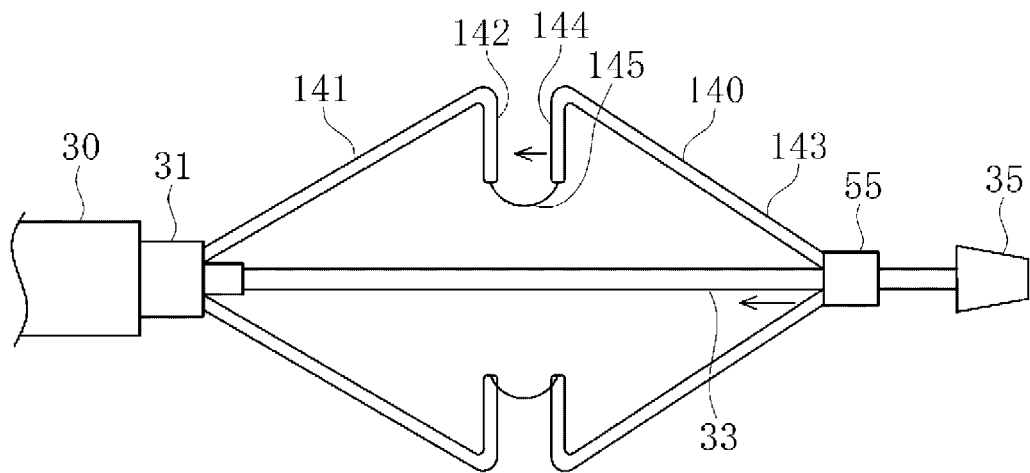
FIG. 19 is an enlarged front view illustrating the vicinity of an expansion body according to a modification example.

The expansion body may be separated on the proximal side and the distal side. As illustrated in FIG. 19, an expansion body 140 has two independent members including a proximal side expansion portion 141 and a distal side expansion portion 143. The proximal side expansion portion 141 has a proximal side holding portion 142, and the distal side expansion portion 143 has a distal side holding portion 144. The proximal side expansion portion 141 and the distal side expansion portion 143 are linked with each other by a link portion 145, for example, a wire. In this case, as illustrated by an arrow in the drawing, the pulling shaft 33 is moved to the proximal side. Accordingly, the distal side expansion portion 143 moves to the proximal side, thereby shortening a distance between the distal side holding portion 144 and the proximal side holding portion 142. In this manner, the biological tissue can be held by the distal side holding portion 144 and the proximal side holding portion 142.

Figure 20A:
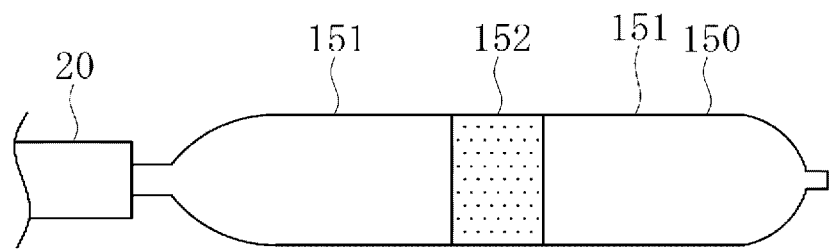
FIGS. 20A and 20B are enlarged front views illustrating each state before expanding and after expanding an expansion body configured to include a balloon, respectively.
Figure 20B:
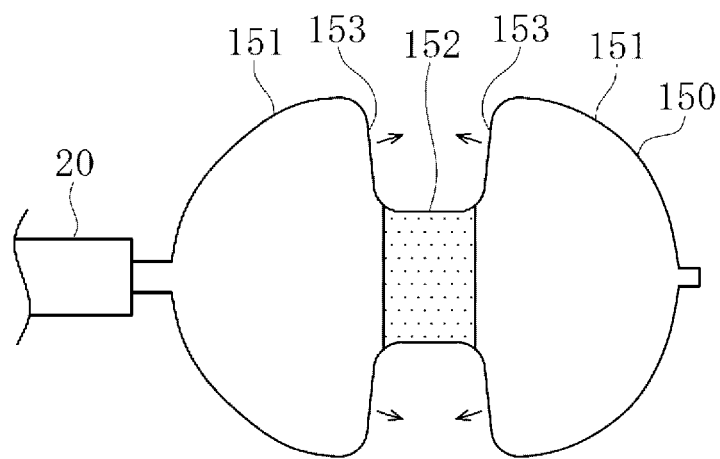

The expansion body can also be formed by using a balloon. In this case, as illustrated in FIG. 20A, a balloon 150 is disposed in the distal portion of the shaft portion 20. In the balloon 150, a region on the distal side and the proximal side in the axial direction is a high compliance portion 151 which is flexible and likely to be inflated. In addition, a region in the central portion in the axial direction of the balloon 150 is a low compliance portion 152 which is relatively hard and less likely to be inflated. When the balloon 150 is inflated, as illustrated in FIG. 20B, a portion of the high compliance portion 151 is inflated, and a portion of the low compliance portion 152 is not inflated as much as the portion of the high compliance portion 151. In this manner, respective surfaces on the central side of the high compliance portion 151 face each other across the low compliance portion 152. The respectively facing surfaces serve as holding portions 153 and 153 which hold the biological tissue.

Figure 21A:
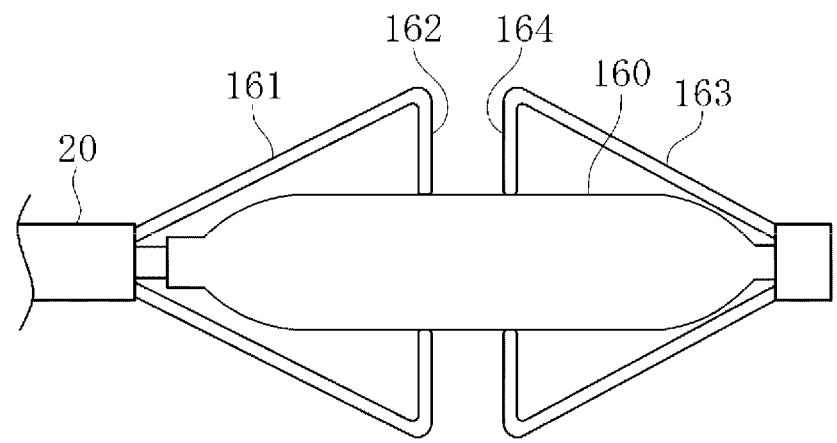
FIGS. 21A and 21B are enlarged front views illustrating each state before expanding and after expanding an expansion body, respectively in which a wire and the balloon are combined with each other.
Figure 21B:
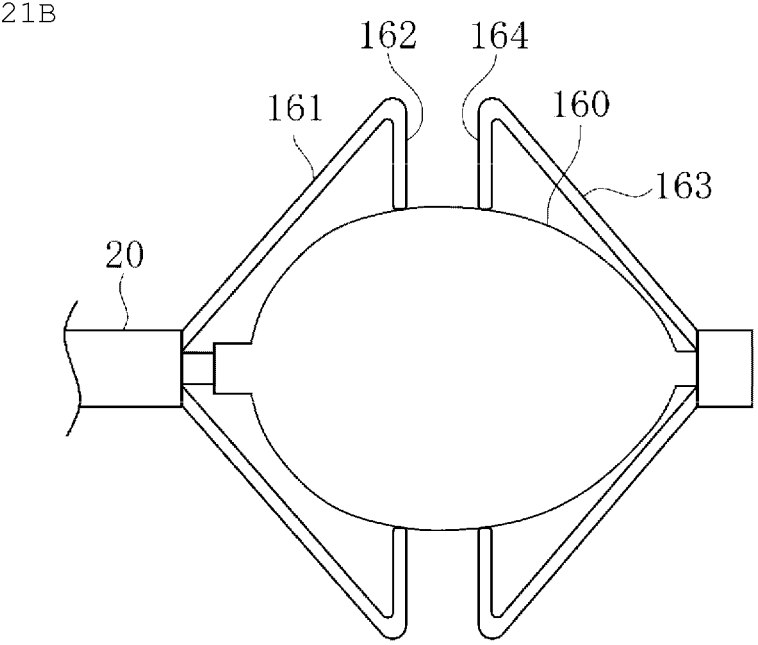

The expansion body may be expanded by using an inflating force of the balloon. In this case, as illustrated in FIG. 21A, the distal portion of the shaft portion 20 has a balloon 160, a proximal side expansion portion 161, and a distal side expansion portion 163. The proximal side expansion portion 161 has a proximal side holding portion 162, and a distal portion of the proximal side holding portion 162 is in contact with the balloon 160. The distal side expansion portion 163 has a distal side holding portion 164, a distal portion of the distal side holding portion 164 is in contact with the balloon 160. When the balloon 160 is inflated, as illustrated in FIG. 21B, the proximal side expansion portion 161 and the distal side expansion portion 163 respectively expand in the radial direction.

Figure 22A:
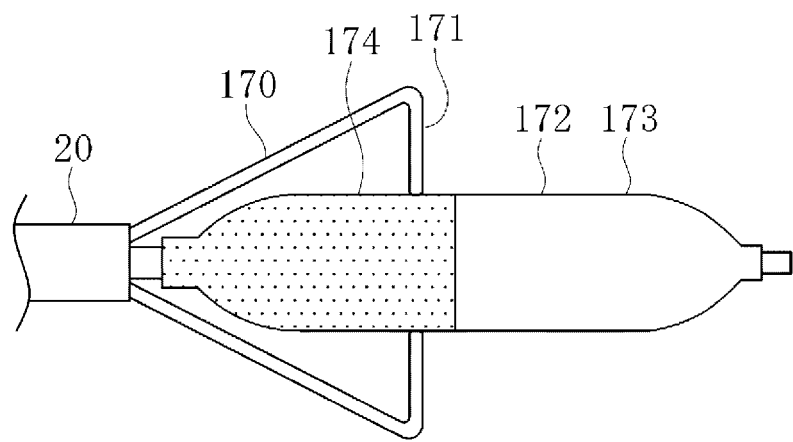
FIGS. 22A and 22B are enlarged front views illustrating each state before expanding and after expanding an expansion body, respectively in which the wire on a proximal side and the balloon are combined with each other.
Figure 22B:
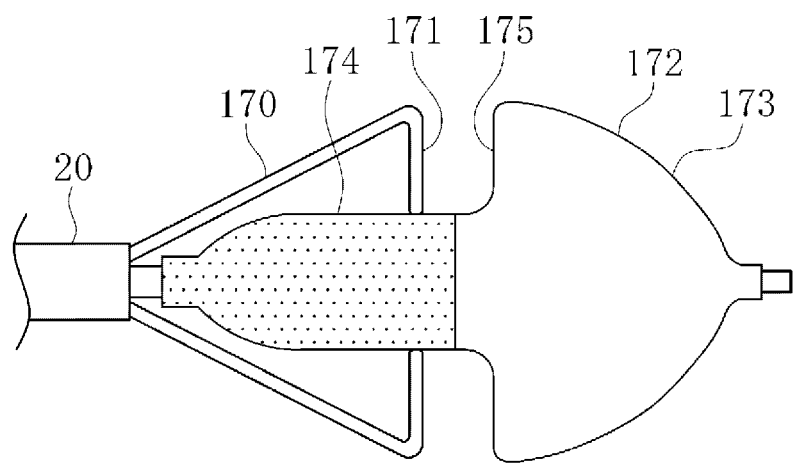

The expansion body may be configured so that the wire and the balloon are combined with each other. In this case, as illustrated in FIG. 22A, the distal portion of the shaft portion 20 has a balloon 172 and a proximal side expansion portion 170. A proximal side holding portion 171 is disposed in the proximal side expansion portion 170. In the balloon 172, a region on the proximal side is a low compliance portion 174 which is relatively hard and less likely to be inflated, and a region on the distal side is a high compliance portion 173 which is relatively flexible and more likely to be inflated. When the balloon 172 is inflated, as illustrated in FIG. 22B, a portion of the high compliance portion 173 which is more likely to be inflated in the balloon 172 is greatly inflated, and a surface on the proximal side faces the proximal side holding portion 171 of the proximal side expansion portion 170. This portion serves as a distal side holding portion 175 that holds the biological tissue.

Modification Example of Expansion Body Disposing Method

Figure 23A:
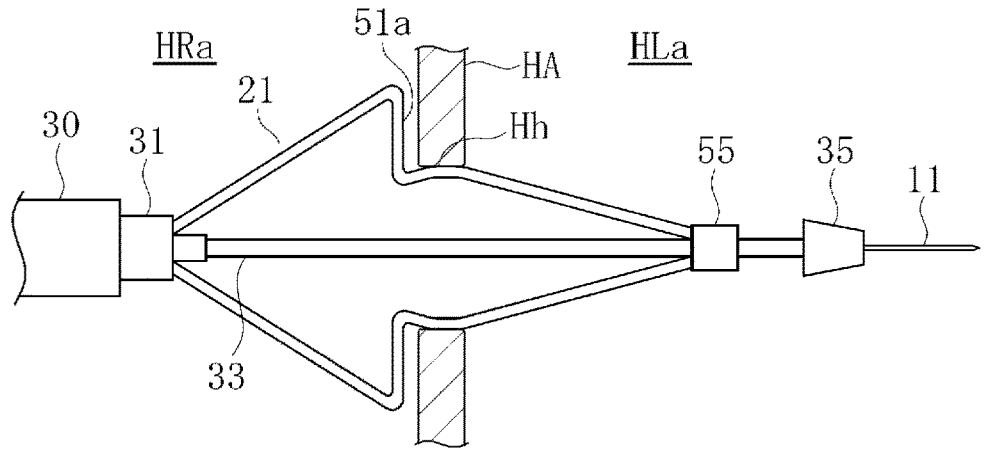
FIGS. 23A-23C are views for schematically describing a step of disposing an expansion body in a treatment method according to a first modification example, in which the biological tissue is illustrated in a sectional view and the medical device is illustrated in a front view, respectively.

In the above-described embodiment, when the expansion body 21 is expanded, the distal side is first expanded, and thereafter, the proximal side is expanded to hold the atrial septum HA. In contrast, the proximal side of the expansion body 21 can be first expanded, and thereafter, the distal side can be expanded to hold the atrial septum HA. In this case, as illustrated in FIG. 23A, in a state where a slightly distal side of the recessed portion 53 in the expansion body 21 is located inside the through-hole Hh, the storage sheath 30 is moved to the proximal side so that the whole expansion body 21 is exposed. In this manner, the through-hole Hh suppresses expansion in the distal side portion from the recessed portion 53 of the expansion body 21, and a portion on the proximal side from the recessed portion 53 of the expansion body 21 is brought into an expanded state in the radial direction.

Figure 23B:
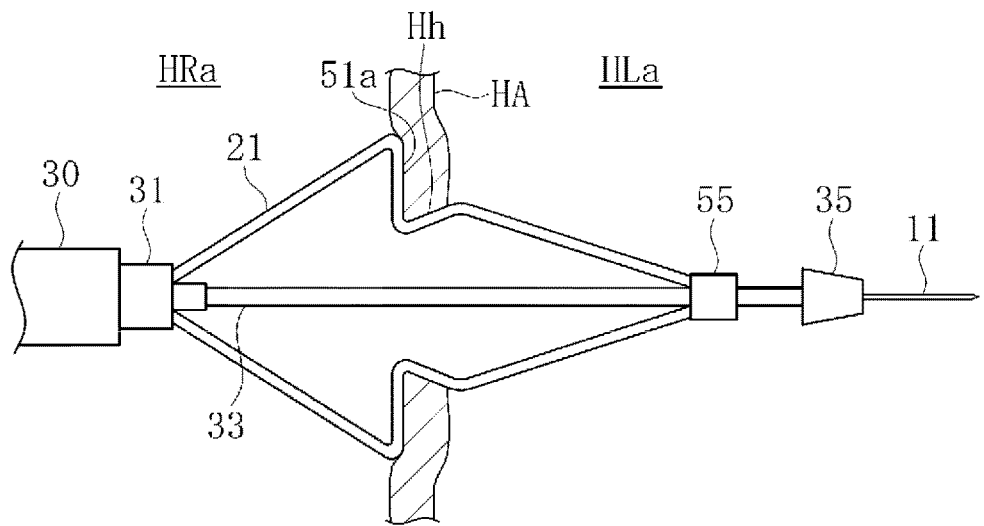
Figure 23C:
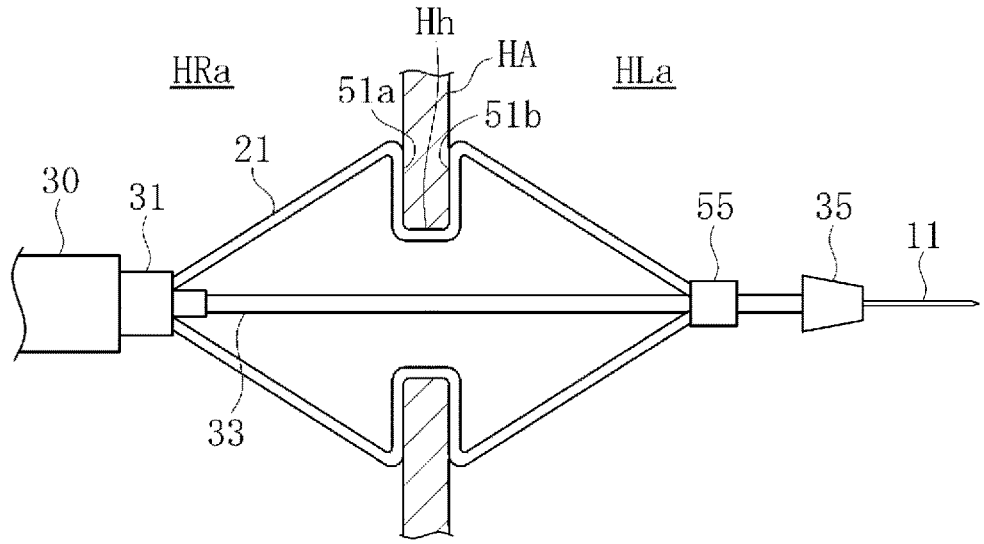

Next, as illustrated in FIG. 23B, the expansion body 21 is moved to the distal side, and the proximal side holding portion 51a of the expansion body 21 is pressed against the atrial septum HA. In this manner, a portion on the distal side of the expansion body 21 enters the inside of the left atrium HLa. In this manner, the portion on the distal side of the expansion body 21 expands in the radial direction. As illustrated in FIG. 23C, the atrial septum HA is brought into a held state by the proximal side holding portion 51a and the distal side holding portion 51b.

Figure 24A:
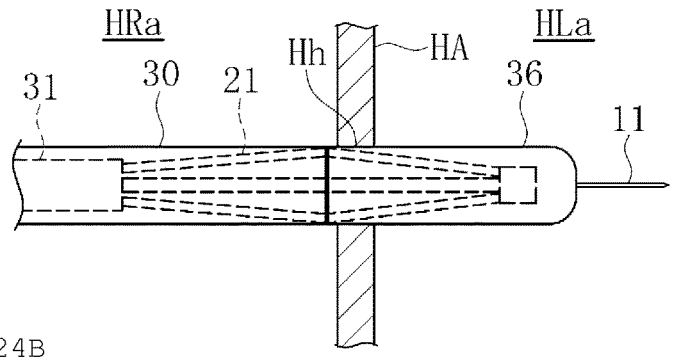
FIGS. 24A-24D are views for schematically describing a step of disposing an expansion body in a treatment method according to a second modification example, in which the biological tissue is illustrated in a sectional view and the medical device is illustrated in a front view, respectively.

In addition, in the method in which the proximal side of the expansion body 21 is first expanded, and thereafter, the distal side is expanded to hold the atrial septum HA, a distal side sheath 36 may be used. In this case, as illustrated in FIG. 24A, the shaft portion 20 has the storage sheath 30 and the distal side sheath 36. The distal side sheath 36 is movable along the axial direction independently of the storage sheath 30. In the expansion body 21, the proximal side is stored in the storage sheath 30, and the distal side is stored in the distal side sheath 36. The shaft portion 20 is inserted until the proximal portion of the distal side sheath 36 is located inside the through-hole Hh.

Figure 24B:
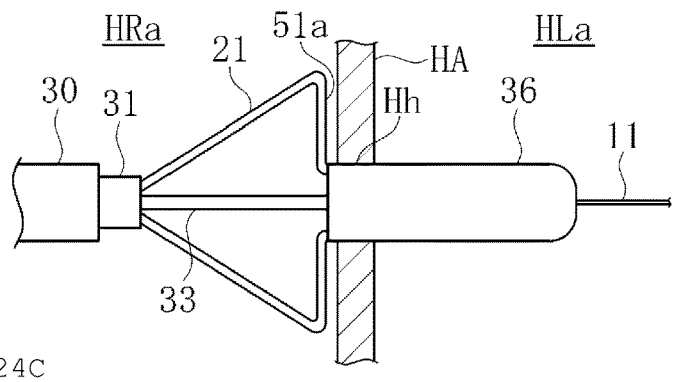
Figure 24C:
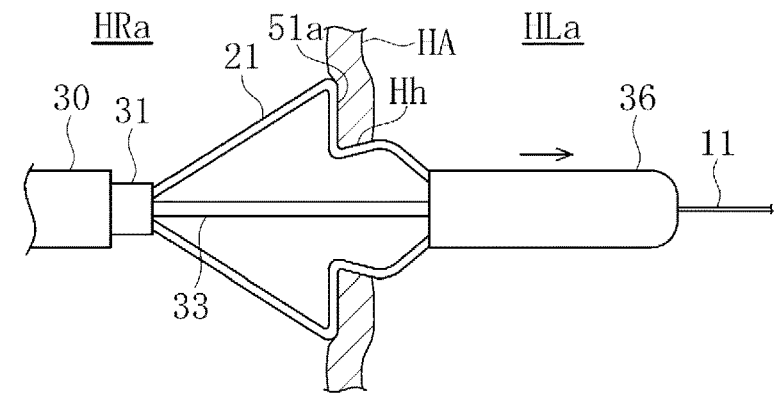
Figure 24D:
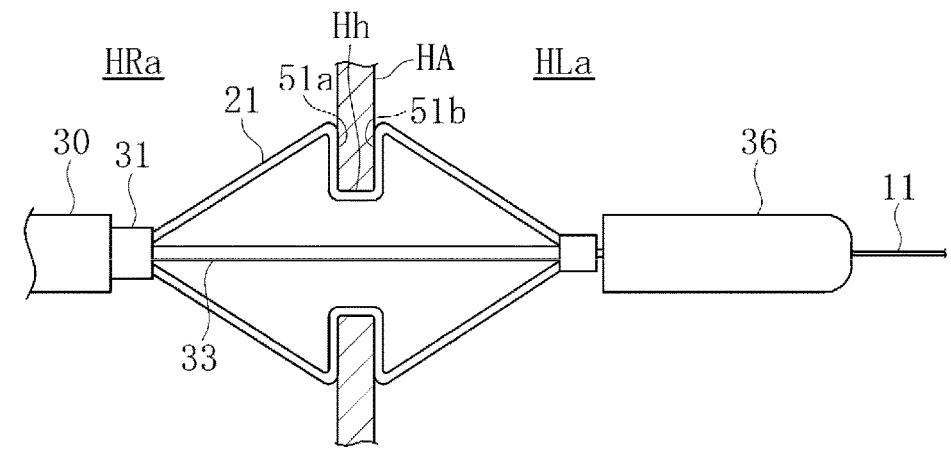

Next, as illustrated in FIG. 24B, the storage sheath 30 is moved to the proximal side so that a portion on the proximal side is exposed from the recessed portion 53 of the expansion body 21. In this manner, the portion on the proximal side from the recessed portion 53 of the expansion body 21 expands in the radial direction. Subsequently, as illustrated in FIG. 24C, the expansion body 21 is moved to the distal side, and the proximal side holding portion 51a of the expansion body 21 is pressed against the atrial septum HA. Thereafter, the distal side sheath 36 is moved toward the distal side. The distal side sheath 36 is moved to the distal side of the distal end of the expansion body 21. Accordingly, as illustrated in FIG. 24D, a portion on the distal side of the expansion body 21 also expands in the radial direction. In this manner, the proximal side holding portion 51a and the distal side holding portion 51b hold the atrial septum HA.

As described above, the medical device 10 according to the above-described embodiment includes the elongated shaft portion 20 and the expansion body 21 disposed in the distal portion of the shaft portion 20 and configured to expand and contract in the radial direction. The expansion body 21 has the holding portion 51 having the proximal side holding portion 51a and the distal side holding portion 51b which hold the biological tissue, and the movable portion 52 that opens and closes the holding portion 51 in the holding direction. In this manner, in the medical device 10 according to the present embodiment, the biological tissue is held from both sides by the holding portion 51 that can be opened and closed in the holding direction. Therefore, it is possible to suppress the positional displacement of the expansion body 21.

In addition, when the movable portion 52 is disposed between the holding portions 51a and 51b on both sides so that the holding portion 51 is opened and closed in a fan shape, the holding portion 51 can be opened and closed using a simple mechanism.

In addition, when the movable portion 52 adopts the bending portion 54 having bending strength different from that of the holding portion 51, the holding portion 51 and the movable portion 52 can be formed by using one wire. Accordingly, a simple structure can be adopted.

In addition, when the movable portion 117 has a rotary shaft portion 118a which enables the holding portions 116 to pivot relative to each other, mobility of the holding portions 116 can be improved, and the holding portions 116 can more reliably hold the biological tissue.

In addition, when the movable portion 123 has the parallel movement portion 126 that moves at least one of the facing holding portions 127 along the axial direction, the biological tissue can be easily held by moving the holding portion 127 in parallel.

In addition, when the shaft portion 20 has the pulling shaft 33 connected to the expansion body 21 to move the distal portion of the expansion body 21 with respect to the proximal portion of the expansion body 21 in the axial direction, a state of the expansion body can be easily operated by operating the pulling shaft 33 with the hand-side portion.

In addition, when the pulling shaft 33 moves the distal portion of the expansion body 21 to the proximal portion side so that the holding portion 51 moves in the expanding direction, the diameter of the expansion body 21 can be enlarged by operating the pulling shaft 33. Accordingly, it is possible to enlarge the diameter of the through-hole Hh.

In addition, when the pulling shaft 33 moves the distal portion of the expansion body 21 to the proximal portion side so that the holding portion 51 is closed in the holding direction, the holding portion 51 can hold the biological tissue by operating the pulling shaft 33.

In addition, when the holding portion 51 further has the restriction element 30 that maintains an open state of the holding portion 51, and the restriction element 30 is released so that the holding portion 51 is closed in the holding direction, the holding portion 51 can rather easily hold the biological tissue by operating the restriction element 30.

In addition, when the holding portion 51 has the maintenance treatment element 22 that performs the maintenance treatment on the biological tissue, the maintenance treatment element 22 is disposed in the holding portion 51 that holds the biological tissue. Therefore, it is possible to suppress the positional displacement of the maintenance treatment element 22.

In addition, in the treatment method according to the above-described embodiment, the through-hole Hh of the biological tissue is enlarged using the medical device 10 having the expansion body 21 configured to expand and contract in the radial direction. The treatment method includes positioning the holding portion 51 of the expansion body 21 in the through-hole Hh of the biological tissue, holding the biological tissue from both sides of the through-hole Hh by using the holding portion 51, enlarging the diameter of through-hole Hh by expanding the expansion body 21, and performing the maintenance treatment by using the maintenance treatment element 22 of the holding portion 51. In this manner, the maintenance treatment is performed in a state where the holding portion 51 holds the biological tissue. Accordingly, while the positional displacement of the maintenance treatment element is suppressed, the energy can be accurately applied to a target site.

In addition, when the holding of the biological tissue by using the holding portion 51 is performed before, after, or simultaneously with the enlarging of the diameter of the through-hole Hh by expanding the expansion body 21, the holding portion 51 can hold the biological tissue at any desired timing. Therefore, it is possible to suppress the positional displacement of the expansion body 21 during the maintenance treatment.

The present disclosure is not limited to the above-described embodiments, and various modifications can be made by those skilled in the art within the technical idea of the present disclosure.

For example, the movable portion 52 of the expansion body 21 may be shaped in advance in the direction in which the holding portion 51 is closed. In this case, when the storage sheath 30 is moved to the proximal side so that the whole expansion body 21 is exposed outward of the storage sheath 30, the movable portion 52 shaped in advance can automatically move in the direction in which the holding portion 51 is closed. In addition, the pulling shaft 33 can adjust the distance in the axial direction between the proximal side holding portion 51 and the distal side holding portion 51.

In addition, the movable portion 52 may deform due to the elastic force of the biological tissue which acts toward a central axis direction of the medical device 10. In this manner, the biological tissue can be held by moving the holding portion 51.

The detailed description above describes embodiments of a medical device including a maintenance treatment element configured to apply energy to a biological tissue, and a treatment method configured to apply energy to a biological tissue. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. A medical device comprising:
   an elongated shaft portion;
   an expansion body disposed in a distal portion of the shaft portion, the expansion body configured to expand and contract in a radial direction;
   the expansion body including a holding portion, the holding portion including a proximal side holding portion and a distal side holding portion, the proximal side holding portion and the distal side holding portion configured to hold a biological tissue, and a movable portion configured to displace the holding portion in a holding direction configured to hold the biological tissue between the proximal side holding portion and the distal side holding portion;
   the expansion body configured to be stored in a storage sheath in a contracted state and to expand in the radial direction by a self-expanding force of the expansion body when exposed outward of the storage sheath; and
   wherein the movable portion is configured to displace the holding portion in the holding direction when the expansion body expands in the radial direction by the self-expanding force of the expansion body, and to expand in the radial direction with the proximal side holding portion and the distal side holding portion after holding the biological tissue between the proximal side holding portion and the distal side holding portion.

2. The medical device according to claim 1, wherein the movable portion is disposed between the proximal side holding portion and the distal side holding portion, and the movable portion is configured to displace the holding portion from a first state, in which the holding portion being opened in a fan shape centered on the movable portion, to a second state, in which holding portion being closed in the holding direction by bending the movable portion.

3. The medical device according to claim 2, wherein the movable portion is a bending portion having a bending strength different from a bending strength of the proximal side holding portion and the distal side holding portion.

4. The medical device according to claim 2, wherein the movable portion has a rotary shaft portion configured to enable the proximal side holding portion and the distal side holding portion to pivot relative to each other.

5. The medical device according to claim 1, wherein the movable portion has a parallel movement portion configured to move to at least one of the proximal side holding portion and the distal side holding portion along an axial direction.

6. The medical device according to claim 1, wherein the shaft portion has a pulling shaft connected to the expansion body to move a distal portion of the expansion body to a proximal portion of the expansion body in an axial direction.

7. The medical device according to claim 6, wherein the distal portion of the expansion body is configured to move to a proximal portion side by the pulling shaft so that the proximal side holding portion and the distal side holding portion move in an expanding direction.

8. The medical device according to claim 6, wherein the distal portion of the expansion body is configured to move to a proximal portion side by the pulling shaft so that the proximal side holding portion and the distal side holding portion are closed.

9. The medical device according to claim 1, further comprising:
   a restriction element configured to maintain a state where the proximal side holding portion and the distal side holding portion are open; and
   wherein the restriction element is configured to be released so that the proximal side holding portion and the distal side holding portion are closed.

10. The medical device according to claim 1, wherein the proximal side holding portion and the distal side holding portion have a maintenance treatment element configured to perform a maintenance treatment on the biological tissue.

11. A treatment method of enlarging a through-hole of an atrial septum by using a medical device having an expansion body that is configured to expand and contract in a radial direction and includes a distal side expansion portion and a proximal side expansion portion, the method comprising:
    expanding the distal side expansion portion of the expansion body in a radial direction inside a left atrium;
    positioning a distal side holding portion of the distal side expansion portion to face a surface on a left atrium side of the atrial septum so as to dispose a movable portion of the expansion body in the through-hole of the atrial septum, the movable portion of the expansion body linking the distal side holding portion and a proximal side holding portion of the proximal side expansion portion and forming a recessed portion with the proximal side holding portion and the distal side holding portion;
    expanding the proximal side holding portion in the radial direction inside a right atrium so as to hold the atrial septum from both sides of the through-hole by the recessed portion;
    expanding the movable portion, the distal side expansion portion and the proximal side expansion portion in the radial direction with holding the atrial septum from both sides of the through-hole by the recessed portion so as to enlarge a diameter of the through-hole by expanding the expansion body; and
    performing a maintenance treatment to the atrial septum held by the recessed portion by using a maintenance treatment element disposed on the recessed portion while the through-hole has been enlarged.

12. The treatment method according to claim 11, further comprising:
    holding the atrial septum between the proximal side holding portion and the distal side holding portion by expanding the proximal side holding portion in the radial direction inside the right atrium.

13. The treatment method according to claim 12, further comprising:
pivoting the proximal side holding portion and the distal side holding portion relative to each other with the movable portion to the hold the atrial septum.

14. The treatment method according to claim 11, further comprising:
delivering the expansion body in a contracted state to the atrial septum within a storage sheath;
removing the expansion body with the contracted state from the storage sheath; and
moving the distal side expansion portion toward the proximal side expansion portion in an axial direction to expand the movable portion, the distal side expansion portion, and the proximal side expansion portion in the radial direction.

15. The treatment method according to claim 14, further comprising:
moving the distal side expansion portion to the proximal side expansion portion with a pulling shaft and moving the proximal side expansion portion and the distal side expansion portion in the axial direction so as to expand the movable portion, the distal side expansion portion and the proximal side expansion portion in the radial direction; and/or
moving the distal side expansion portion to the proximal portion side expansion portion with the pulling shaft and moving the proximal side expansion portion and the distal side expansion portion in the axial direction towards one another so as to expand the movable portion, the distal side expansion portion and the proximal side expansion portion in the radial direction.

16. The treatment method according to claim 11, further comprising:
disposing the movable portion of the expansion body in the through-hole of the atrial septum by pressing the distal side holding portion to the surface on the left atrium side of the atrial septum.

17. The treatment method according to claim 11, further comprising:
delivering the expansion body in a contracted state to the atrial septum within a storage sheath; and
removing the expansion body with the contracted state from the storage sheath so as to expand the distal side expansion portion in the radial direction inside the left atrium and the proximal side holding portion in the radial direction inside the right atrium, to dispose the movable portion in the through-hole of the atrial septum and to hold the atrial septum from both sides of the through-hole by the recessed portion, while not expanding the movable portion to be larger than an outer diameter of the storage sheath so as not to substantially enlarge the through-hole.

18. A medical device comprising:
an elongated shaft portion;
an expansion body disposed in a distal portion of the shaft portion, the expansion body including a plurality of wires in a circumferential direction, each of the plurality of wires configured to expand and contract in a radial direction;
each of the plurality of wires comprising:
a proximal side expansion portion extending radially in a distal direction from a proximal portion of the expansion body;
a distal side expansion portion extending radially in a proximal direction from a distal portion of the expansion body; and
a recessed portion disposed between the proximal side expansion portion and the distal side expansion portion and recessed radially inward;
the recessed portion of each of the plurality of wires comprising:
a proximal side erected portion connected to a distal end of the proximal side expansion portion;
a bottom portion disposed innermost of the recessed portion and distal of the proximal side erected portion; and
a distal side erected portion disposed distal of the bottom portion and connected to the distal side expansion portion; and
wherein the expansion body is configured to expand to a first expanded state by a self-expanding force such that the bottom portion moves radially outward, and the proximal side erected portion and the distal side erected portion move closer to each other, and the expansion body is configured to expand a second expanded state further expanding than the first expanded state by the bottom portion, the proximal side expansion portion and distal side expansion portion moving radially outward.

19. A treatment method of enlarging a through-hole of a biological tissue by using a medical device having an expansion body having a plurality of wires in a circumferential direction, each of the plurality of wires configured to expand and contract in a radial direction, the method comprising:
expanding a distal side expansion portion of the expansion body in the radial direction at a one side of the biological tissue and a proximal side expansion portion of the expansion body in the radial direction at an opposite side of the biological tissue opposed to the one side so as to position a recessed portion of each of the plurality of wires of the expansion body in the through-hole of the biological tissue and to receive the biological tissue in the recessed portion;
enlarging a diameter of the through-hole with receiving the biological tissue in the recessed portion by the bottom portion of the recessed portion expanding radially outward into the biological tissue and the distal side expansion portion and the proximal side expansion portion expanding radially outward at both sides of the biological tissue; and
performing a maintenance treatment to the biological tissue received in the recessed portion by using a maintenance treatment element disposed on the recess portion of the expansion body.

20. The treatment method according to claim 19, wherein each of the plurality of wires comprises a proximal side expansion portion extending radially in a distal direction from a proximal portion of the expansion body, and the recessed portion disposed distal of the proximal side expansion and recessed radially inward, and wherein the recessed portion of each of the plurality of wires includes a proximal side erected portion connected to a distal end of the proximal side expansion portion, the bottom portion disposed innermost of the recessed portion and distal of the proximal side erected portion, and a distal side erected portion disposed distal of the bottom portion, the method further comprising:
moving the proximal side erected portion and the distal side erected portion move closer to each other as the bottom portion moves radially outward.

* * * * *